(12) United States Patent
Askegaard et al.

(10) Patent No.: US 11,918,460 B2
(45) Date of Patent: Mar. 5, 2024

(54) PROSTHETIC HEART VALVES

(71) Applicant: Laplace Interventional Inc., Plymouth, MN (US)

(72) Inventors: Gunnar Paul Askegaard, Champlin, MN (US); Lucas Tradd Schneider, Champlin, MN (US); Ramji Iyer, Plymouth, MN (US)

(73) Assignee: Laplace Interventional Inc., Plymouth, MN (US)

( * ) Notice: Subject to any disclaimer, the term of this patent is extended or adjusted under 35 U.S.C. 154(b) by 0 days.

(21) Appl. No.: 18/244,015

(22) Filed: Sep. 8, 2023

(65) Prior Publication Data

US 2024/0024096 A1 Jan. 25, 2024

Related U.S. Application Data

(60) Continuation of application No. 18/124,684, filed on Mar. 22, 2023, now Pat. No. 11,759,316, which is a division of application No. 17/986,607, filed on Nov. 14, 2022, now Pat. No. 11,638,643.

(60) Provisional application No. 63/390,810, filed on Jul. 20, 2022.

(51) Int. Cl.
*A61F 2/24* (2006.01)

(52) U.S. Cl.
CPC .......... *A61F 2/2403* (2013.01); *A61F 2/2418* (2013.01); *A61F 2/2436* (2013.01); *A61F 2/246* (2013.01); *A61F 2230/0008* (2013.01)

(58) Field of Classification Search
CPC .... A61F 2/2436; A61F 2/2403; A61F 2/2418; A61F 2/246; A61F 2230/0008
See application file for complete search history.

(56) References Cited

U.S. PATENT DOCUMENTS

| | | |
|---|---|---|
| 5,824,069 A | 10/1998 | Lemole |
| 6,312,464 B1 | 11/2001 | Navia |
| 6,458,153 B1 | 10/2002 | Bailey et al. |
| 8,728,155 B2 | 5/2014 | Montorfano et al. |
| 9,393,110 B2 | 7/2016 | Levi et al. |
| 9,579,196 B2 | 2/2017 | Morriss |
| 9,681,951 B2 | 6/2017 | Ratz et al. |
| 10,213,307 B2 | 2/2019 | Dwork |

(Continued)

FOREIGN PATENT DOCUMENTS

WO   WO 2015/052570   4/2015

*Primary Examiner* — Suzette J Gherbi
(74) *Attorney, Agent, or Firm* — Fish & Richardson P.C.

(57) ABSTRACT

Prosthetic heart valves may be delivered to a targeted native heart valve site via one or more delivery catheters. In some embodiments, the prosthetic heart valve includes structural features that securely anchor the prosthetic heart valve to the anatomy at the site of the native heart valve. Such structural features can provide robust migration resistance. In addition, the prosthetic heart valves can include structural features that improve sealing between the prosthetic valve and native valve anatomy to mitigate paravalvular leakage. In particular implementations, the prosthetic heart valves occupy a small delivery profile, thereby facilitating a smaller delivery catheter system for advancement to the heart. Some delivery catheter systems can include a curved inner catheter to facilitate deployment of the prosthetic heart valve to a native tricuspid valve site via a superior vena cava or inferior vena cava.

26 Claims, 24 Drawing Sheets

(56) References Cited

U.S. PATENT DOCUMENTS

| Patent/Publication | Date | Name | Class |
|---|---|---|---|
| 10,321,995 B1 | 6/2019 | Christianson | |
| 10,583,000 B2 | 3/2020 | Ratz | |
| 10,653,522 B1 | 5/2020 | Vidlund et al. | |
| 10,779,935 B2 * | 9/2020 | Scorsin | A61F 2/2418 |
| 10,779,936 B2 | 9/2020 | Pollak | |
| 10,813,779 B2 | 10/2020 | Fleming, III et al. | |
| 10,898,328 B2 | 1/2021 | Starksen et al. | |
| 11,109,965 B2 | 9/2021 | Iyer et al. | |
| 11,185,409 B2 * | 11/2021 | Christianson | A61F 2/2418 |
| 11,234,813 B2 * | 2/2022 | Perrin | A61F 2/2433 |
| 11,253,359 B2 * | 2/2022 | Vidlund | A61F 2/2439 |
| 11,337,800 B2 | 5/2022 | Schreck et al. | |
| 11,337,801 B2 | 5/2022 | Iyer et al. | |
| 11,344,413 B2 * | 5/2022 | Christianson | A61F 2/2436 |
| 11,504,231 B2 | 11/2022 | Carlino et al. | |
| 11,510,777 B1 * | 11/2022 | Iyer | A61F 2/2418 |
| 11,564,794 B2 | 1/2023 | Straubinger et al. | |
| 11,602,433 B2 * | 3/2023 | Ratz | A61F 2/2463 |
| 11,638,643 B1 * | 5/2023 | Askegaard | A61F 2/2436 623/2.11 |
| 2004/0092962 A1 * | 5/2004 | Thornton | A61B 17/122 606/139 |
| 2005/0149181 A1 | 7/2005 | Eberhardt | |
| 2007/0043435 A1 * | 2/2007 | Seguin | A61F 2/2433 623/2.11 |
| 2007/0055356 A1 | 3/2007 | Eidenschink | |
| 2010/0023046 A1 | 1/2010 | Heidner et al. | |
| 2010/0161045 A1 | 6/2010 | Righini | |
| 2010/0217382 A1 | 8/2010 | Chau et al. | |
| 2010/0316830 A1 | 12/2010 | Hartley et al. | |
| 2011/0137397 A1 | 6/2011 | Chau et al. | |
| 2012/0083832 A1 | 4/2012 | Delaloye et al. | |
| 2013/0211508 A1 | 8/2013 | Lane et al. | |
| 2014/0207231 A1 | 7/2014 | Hacohen et al. | |
| 2014/0222142 A1 | 8/2014 | Kovalsky et al. | |
| 2014/0257467 A1 | 9/2014 | Lane et al. | |
| 2014/0277390 A1 | 9/2014 | Ratz | |
| 2014/0296969 A1 | 10/2014 | Tegels et al. | |
| 2014/0296975 A1 | 10/2014 | Tegels et al. | |
| 2014/0350669 A1 | 11/2014 | Gillespie et al. | |
| 2015/0119981 A1 | 4/2015 | Khairkhahan et al. | |
| 2015/0196390 A1 | 7/2015 | Ma et al. | |
| 2015/0216653 A1 | 8/2015 | Freudenthal | |
| 2015/0327994 A1 | 11/2015 | Morriss et al. | |
| 2016/0158003 A1 | 6/2016 | Wallace et al. | |
| 2016/0278922 A1 | 9/2016 | Braido et al. | |
| 2017/0056166 A1 | 3/2017 | Ratz et al. | |
| 2017/0065409 A1 * | 3/2017 | Scorsin | A61F 2/2418 |
| 2017/0071733 A1 | 3/2017 | Ghione et al. | |
| 2017/0128199 A1 | 5/2017 | Gurovich et al. | |
| 2017/0128208 A1 | 5/2017 | Christianson et al. | |
| 2017/0216023 A1 | 8/2017 | Lane et al. | |
| 2017/0216026 A1 | 8/2017 | Quill et al. | |
| 2017/0325945 A1 | 11/2017 | Dale et al. | |
| 2018/0000586 A1 | 1/2018 | Ganesan | |
| 2019/0008636 A1 | 1/2019 | Francis et al. | |
| 2019/0029811 A1 | 1/2019 | Bishop et al. | |
| 2019/0183639 A1 | 6/2019 | Moore | |
| 2020/0179109 A1 | 6/2020 | Reimer | |
| 2020/0268512 A1 | 8/2020 | Mohl | |
| 2021/0220126 A1 | 7/2021 | Perrin | |
| 2021/0236257 A1 * | 8/2021 | Walzman | A61F 2/2436 |
| 2021/0244535 A1 * | 8/2021 | Iyer | A61F 2/2418 |
| 2021/0290385 A1 | 9/2021 | Christianson et al. | |
| 2021/0315694 A1 | 10/2021 | Vidlund et al. | |
| 2021/0346153 A1 | 11/2021 | Vietmeier et al. | |
| 2021/0393401 A1 | 12/2021 | Iyer et al. | |
| 2021/0401572 A1 | 12/2021 | Nasr | |
| 2022/0096226 A1 * | 3/2022 | Christianson | A61F 2/2439 |
| 2022/0192824 A1 | 6/2022 | Vidlund et al. | |
| 2022/0273427 A1 | 9/2022 | Iyer et al. | |
| 2022/0313428 A1 | 10/2022 | Bergin | |
| 2022/0409369 A1 * | 12/2022 | Christianson | A61F 2/2436 |
| 2023/0130224 A1 | 4/2023 | Rajagopal | |
| 2023/0131595 A1 * | 4/2023 | Van Hoven | A61F 2/246 623/2.11 |
| 2023/0293297 A1 * | 9/2023 | Alon | A61F 2/2418 29/451 |

* cited by examiner

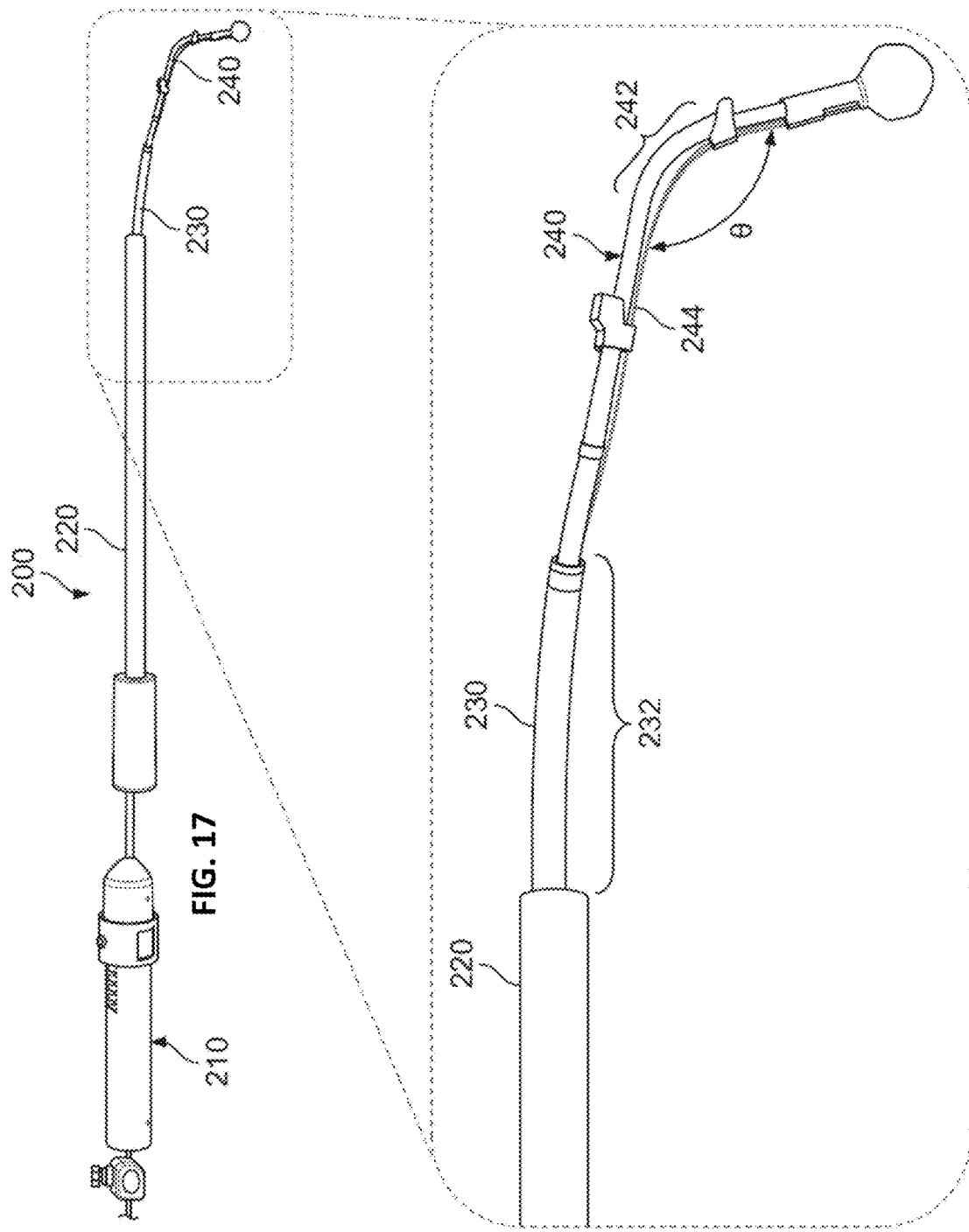

PROSTHETIC HEART VALVES

CROSS-REFERENCE TO RELATED APPLICATIONS

This application is a continuation of U.S. application Ser. No. 18/124,684 filed on Mar. 22, 2023, which is a divisional of U.S. application Ser. No. 17/986,607 filed on Nov. 14, 2022, which claims the benefit of U.S. Provisional Application Ser. No. 63/390,810, filed Jul. 20, 2022. The disclosures of the prior applications are considered part of (and are incorporated by reference in) the disclosure of this application.

FIELD OF INVENTION

This disclosure generally relates to prosthetic heart valve systems. For example, this disclosure relates to transcatheter deliverable prosthetic heart valves that are adapted to be used to replace a sub-optimally functioning native heart valve, including but not limited to a tricuspid valve.

BACKGROUND

A human heart includes four types of heart valves that are arranged to ensure blood flow in specific directions: mitral, tricuspid, aortic and pulmonary valves. The aortic and pulmonary valves are semilunar valves, which are in the arteries leaving the heart, and prevent blood from flowing back into left ventricle and right ventricle respectively when closed. The mitral and tricuspid valves are atrio-ventricular valves, which are between the atria and the ventricles, and prevent blood from flowing back into left atrium and right atrium respectively when closed. Conditions of stenosis (when valve does not open fully) as well as regurgitation/insufficiency (when valve does not close properly resulting in leaks) are recognized as significant contributors to mortality and morbidity.

Some valve replacement systems include valve prostheses that are compressed into a delivery catheter, also referred to as transcatheter valves, so as to avoid open-heart surgery. Many transcatheter valve prostheses have a tubular frame that may or may not be axisymmetric, and include two or more leaflets. While these transcatheter valve prostheses can be compressed into a catheter, they may still require a large delivery system (for example, a required catheter size of 45 French). This is especially true in case of mitral valve replacement systems and tricuspid valve replacement systems, which often require valve prostheses with a larger profile.

SUMMARY

Some embodiments described herein include a prosthetic heart valve that may be delivered to a targeted native heart valve site via one or more delivery catheters. In some embodiments, a prosthetic heart valve includes structural features that securely anchor the prosthetic heart valve to the anatomy at the site of the native heart valve. Such structural features can provide robust migration resistance. In addition, the prosthetic heart valves can include structural features that improve sealing between the prosthetic valve and native valve anatomy to mitigate paravalvular leakage. In particular implementations, the prosthetic heart valves occupy a small delivery profile, thereby facilitating a smaller delivery catheter system for advancement to the heart. Some delivery catheter systems can include a curved inner catheter to facilitate deployment of the prosthetic heart valve to a native tricuspid valve site via a superior vena cava or inferior vena cava.

In one aspect, this disclosure is directed to a prosthetic heart valve that includes a main body comprising an inflow end portion and an outflow end portion, and an occluder extending between the inflow end and outflow end portions and comprising valve leaflets attached to the main body in an arrangement that: (i) allows blood flow through the occluder in a direction from the inflow end portion toward the outflow end portion along a central axis of the occluder and (ii) prevents blood flow through the occluder in a direction from the outflow end portion toward the inflow end portion. The prosthetic heart valve also includes a first anterior flap extending from the outflow end portion in a first direction that is transverse to the central axis; a posterior flap extending from the outflow end portion in a second direction that is opposite of the first direction; and a posterior arm extending from the inflow end portion in the second direction.

Such a prosthetic heart valve may optionally include one or more of the following features. The prosthetic heart valve may also include an anterior arm extending from the inflow end portion in the first direction. The prosthetic heart valve may also include a second anterior flap extending from the outflow end portion in the first direction. The first and second anterior flaps may overlap each other. A cross-sectional shape of the first and second anterior flaps taken perpendicularly to the first direction may be arcuate.

In another aspect, this disclosure is directed to another prosthetic heart valve. The prosthetic heart valve includes a main body comprising an inflow end portion and an outflow end portion, and an occluder extending between the inflow end and outflow end portions and comprising valve leaflets attached to the main body in an arrangement that: (i) allows blood flow through the occluder in a direction from the inflow end portion toward the outflow end portion along a central axis of the occluder and (ii) prevents blood flow through the occluder in a direction from the outflow end portion toward the inflow end portion. The prosthetic heart valve also includes an anterior flap extending from the outflow end portion in a first direction that is transverse to the central axis; a posterior flap extending from the outflow end portion in a second direction that is opposite of the first direction; and an anterior arm extending from the inflow end portion in the first direction.

In another aspect, this disclosure is directed to another prosthetic heart valve. The prosthetic heart valve includes a main body comprising an inflow end portion and an outflow end portion, and an occluder extending between the inflow end and outflow end portions and comprising valve leaflets attached to the main body in an arrangement that: (i) allows blood flow through the occluder in a direction from the inflow end portion toward the outflow end portion along a central axis of the occluder and (ii) prevents blood flow through the occluder in a direction from the outflow end portion toward the inflow end portion. The prosthetic heart valve also includes a first anterior flap extending from the outflow end portion in a first direction that is transverse to the central axis; and a second anterior flap extending from the outflow end portion in the first direction. A cross-sectional shape of the first and second anterior flaps taken perpendicularly to the first direction is arcuate from an outer edge of the first anterior flap to an outer edge of the second anterior flap.

In another aspect, this disclosure is directed to another prosthetic heart valve. The prosthetic heart valve includes a main body comprising an inflow end portion and an outflow end portion, and an occluder extending between the inflow end and outflow end portions and comprising valve leaflets attached to the main body in an arrangement that: (i) allows blood flow through the occluder in a direction from the inflow end portion toward the outflow end portion along a central axis of the occluder and (ii) prevents blood flow through the occluder in a direction from the outflow end portion toward the inflow end portion. The prosthetic heart valve also includes a first anterior flap extending from the outflow end portion in a first direction that is transverse to the central axis: a second anterior flap extending from the outflow end portion in the first direction; a first posterior flap extending from the outflow end portion in a second direction that is opposite of the first direction; and a second posterior flap extending from the outflow end portion in the second direction. A passageway is defined between the first and second posterior flaps. The first and second posterior flaps extend from the outflow end portion farther than the first and second anterior flaps.

In another aspect, this disclosure is directed to a method of deploying a prosthetic heart valve. The method includes engaging any of the prosthetic heart valves described herein with anatomical structures of a native tricuspid valve. The lateral anterior flap extends into a right ventricular outflow tract (RVOT) and engages with a lateral wall of the RVOT to provide anchoring during diastole.

In another aspect, this disclosure is directed to another method of deploying a prosthetic heart valve. The method includes engaging any of the prosthetic heart valves described herein with anatomical structures of a native tricuspid valve. A distal end portion of the posterior arm rests against an interior wall of an inferior vena cava, or coronary sinus, or a right atrium.

In another aspect, this disclosure is directed to another method of deploying a prosthetic heart valve. The method includes engaging any of the prosthetic heart valves described herein with anatomical structures of a native tricuspid valve. A distal end portion of the anterior arm rests against an interior wall of a right atrial appendage.

Various types of deployment systems may be used in combination with the prosthetic tricuspid valves described herein. In some embodiments described herein, such a deployment system may include an outer sheath catheter defining a first lumen; a middle deflectable catheter slidably disposed in the first lumen and defining a second lumen, the middle deflectable catheter comprising a selectively deflectable distal end portion with at least one plane of deflection; and an inner control catheter slidably disposed in the second lumen and including one or more control wires that configure the inner control catheter to releasably couple with a prosthetic heart valve. The inner control catheter includes a distal end portion that elastically transitions to a naturally curved configuration when the inner control catheter converts from being radially constrained to being radially unconstrained. In some embodiments, the distal end portion defines an interior angle of less than 135 degrees when in the naturally curved configuration.

In another aspect, this disclosure is directed to another method of deploying a prosthetic heart valve. The method includes advancing the prosthetic heart valve toward a native tricuspid valve, via a jugular vein and a superior vena cava, while the prosthetic heart valve is releasably coupled to a prosthetic heart valve deployment system and diametrically constrained in a low profile delivery configuration. The prosthetic heart valve deployment system includes an outer sheath catheter defining a first lumen; a middle deflectable catheter slidably disposed in the first lumen and defining a second lumen, the middle deflectable catheter comprising a selectively deflectable distal end portion; and an inner control catheter slidably disposed in the second lumen and including one or more control wires that are releasably coupled with the prosthetic heart valve. The inner control catheter includes a distal end portion constrained in the first lumen. The method also includes retracting the outer sheath relative to the inner control catheter to allow the distal end portion of the inner control catheter to become radially unconstrained and to elastically transition to a curved configuration; and deflecting the selectively deflectable distal end portion of the middle deflectable catheter so that the inner control catheter and the middle deflectable catheter in combination are curved by at least 90° relative to the outer sheath.

In another aspect, this disclosure is directed to a prosthetic heart valve deployment system that includes an outer sheath catheter defining a first lumen; a middle deflectable catheter slidably disposed in the first lumen and defining a second lumen, the middle deflectable catheter comprising a selectively deflectable distal end portion with at least one plane of deflection; and an inner control catheter slidably disposed in the second lumen and including one or more control wires that configure the inner control catheter to releasably couple with a prosthetic heart valve. The inner control catheter includes a distal end portion that elastically transitions to a naturally curved configuration when the inner control catheter converts from being radially constrained to being radially unconstrained.

In another aspect, this disclosure is directed to another method of deploying a prosthetic heart valve. The method includes advancing the prosthetic heart valve toward a native tricuspid valve, via a femoral vein and an inferior vena cava, while the prosthetic heart valve is releasably coupled to a prosthetic heart valve deployment system and diametrically constrained in a low profile delivery configuration. The prosthetic heart valve deployment system includes an outer sheath catheter defining a first lumen; a middle deflectable catheter slidably disposed in the first lumen and defining a second lumen, the middle deflectable catheter comprising a selectively deflectable distal end portion; and an inner control catheter slidably disposed in the second lumen and including one or more control wires that are releasably coupled with the prosthetic heart valve. The inner control catheter includes a curved distal end portion that is curved by less than 20° when constrained in the first lumen. The method also includes advancing the inner control catheter relative to the outer sheath to allow the curved distal end portion to become unconstrained and to elastically transition to a curved configuration that is curved by at least 45° relative to the outer sheath; and deflecting the selectively deflectable distal end portion of the middle deflectable catheter so that the inner control catheter and the middle deflectable catheter in combination are curved by at least 90° relative to the outer sheath.

Any of the prosthetic heart valves described herein may optionally include one or more of the following additional features. In some embodiments, portions of the first anterior flap and the second anterior flap overlap each other. The prosthetic tricuspid valve may also include a posterior flap extending laterally from the end of the main body in an opposite direction as the first and second anterior flaps. In some embodiments, the first and second anterior flaps extend farther laterally than the posterior flap. In particular embodiments, the first and second anterior flaps in combination are wider (in the septal to lateral direction) than the posterior flap. A framework of the prosthetic tricuspid valve (that comprises the main body, the first and second anterior flaps, and the posterior flap) may be made of a single, unitary material that was cut and expanded. In some embodiments, a distal tip portion of the posterior flap extends along an axis that is at a non-zero angle relative to a portion of the posterior flap that extends directly from the main body. In some examples, having the portions of the first anterior flap and the second anterior flap that overlap each other increases a bending resistance of the first anterior flap and the second anterior flap in combination as compared to the first anterior flap and the second anterior flap individually. Having the portions of the first anterior flap and the second anterior flap as separate members can configure the prosthetic tricuspid valve to have a pacemaker lead pass through the prosthetic tricuspid valve between the first and second anterior flaps. The prosthetic tricuspid valve may also include one or more additional anterior flaps extending laterally from the end of the main body in the same direction as the first and second anterior flaps. The prosthetic tricuspid valve may also include two or more posterior flaps extending laterally from the end of the main body in an opposite direction as the first and second anterior flaps. Having the portions of the first posterior flap and the second posterior flap as separate members can configure the prosthetic tricuspid valve to have a pacemaker lead pass through the prosthetic tricuspid valve between the first and second posterior flaps. In some embodiments, a transverse cross-section of the main body has an oval shaped outer profile that defines a major diameter and a minor diameter. The minor diameter is shorter than the major diameter. The occluder may have a circular cross-sectional shape, and the anterior and posterior flaps may extend transversely to the major diameter. The prosthetic heart valve may also include a leaflet engagement member extending from the main body, a portion of the leaflet engagement member extending toward the inflow end portion and terminating at a free end. The leaflet engagement member may extend in the second direction. The posterior flap may extend farther away from the main body than the leaflet engagement member.

BRIEF DESCRIPTION OF FIGURES

FIG. 17 shows a plan view of an example prosthetic heart valve deployment system in accordance with some embodiments.

FIG. 18 shows an expanded view of a distal end portion of the prosthetic heart valve deployment system of FIG. 17.

DETAILED DESCRIPTION

Some embodiments described herein include a prosthetic heart valve that may be delivered to a targeted native heart valve site via one or more delivery catheters. In some embodiments, a prosthetic heart valve includes structural features that securely anchor the prosthetic heart valve to the anatomy at the site of the native heart valve. Such structural features can provide robust migration resistance during diastole and systole. In addition, the prosthetic heart valves can include structural features that improve sealing between the prosthetic valve and native valve anatomy to mitigate paravalvular leakage. In particular implementations, the prosthetic heart valves occupy a small delivery profile, thereby facilitating a smaller delivery catheter system for advancement to the heart. Some catheter-based prosthetic heart valve deployment systems can include a curved inner catheter to facilitate deployment of the prosthetic heart valve to a native tricuspid valve site via a superior vena cava or inferior vena cava.

Figure 1:
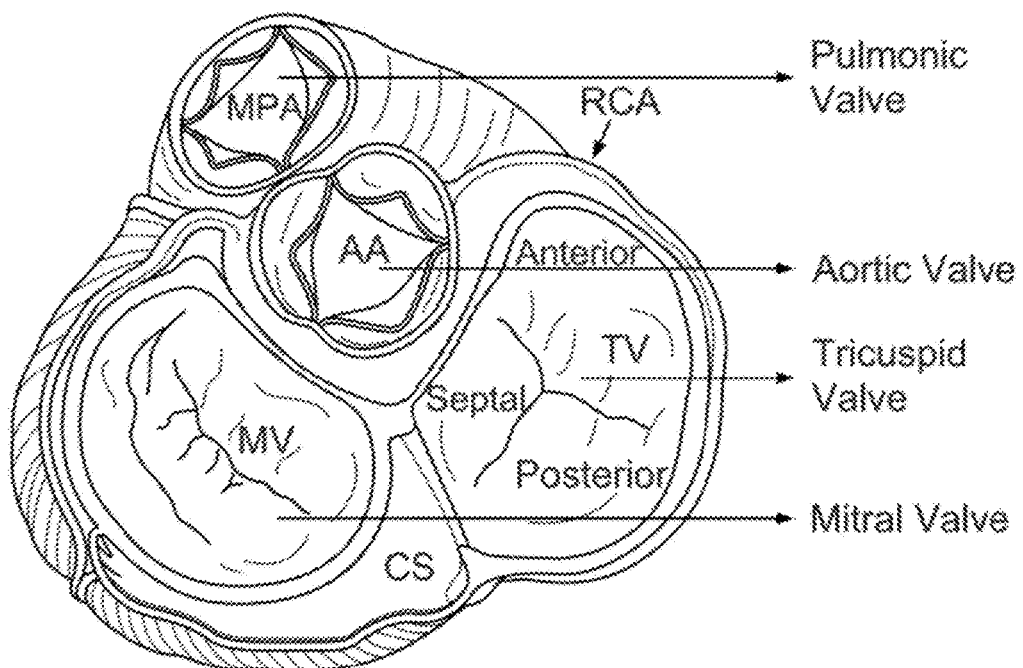
FIG. 1 shows a sectional view of a human heart including four heart valves (mitral valve, tricuspid valve, aortic valve, and pulmonary valve) that allow blood flow through specific pathways. The mitral and tricuspid valve are arranged to prevent backflow of blood into left atrium and right atrium respectively when the left and right ventricle contract respectively.
Figure 2:
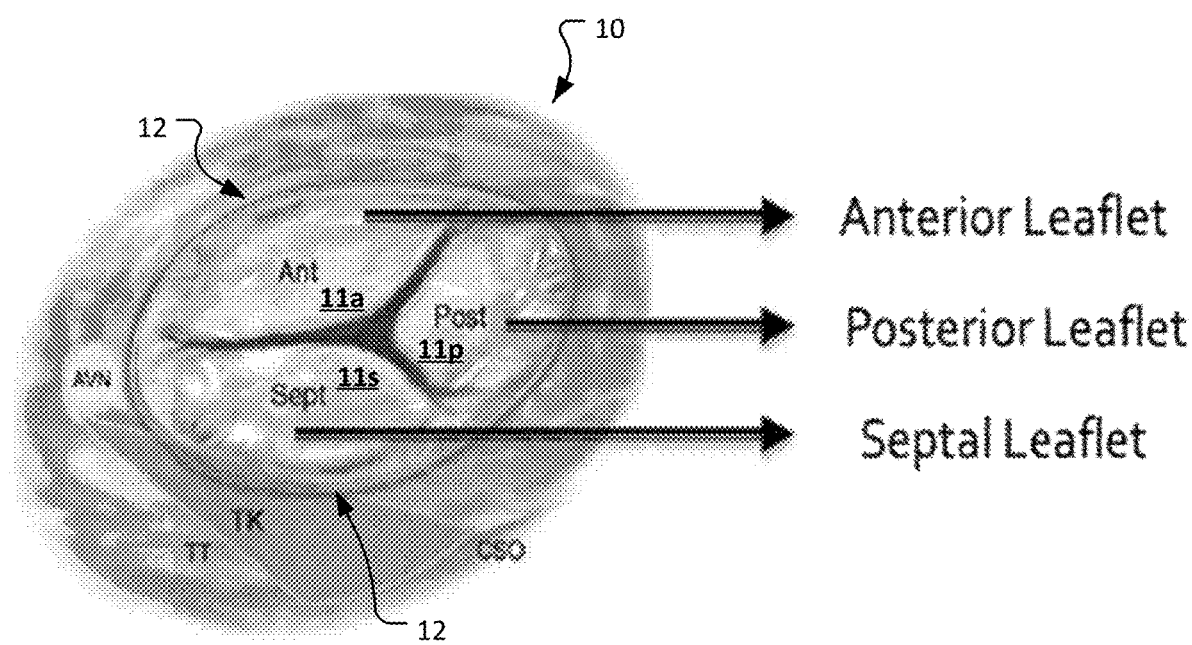
FIG. 2 shows a top view of the tricuspid valve of FIG. 1 and including three native leaflets: anterior, posterior and septal.

Referring to FIG. 1, certain aspects of the concepts described herein regarding the heart valve replacement systems can be implemented in prosthetic valve designs that are intended for use at any of the four heart valves that allow blood flow through a specific pathway: mitral valve, tricuspid valve, aortic valve and the pulmonary valve. FIG. 2 depicts, for example, a targeted site at a tricuspid valve of the heart. The tricuspid valve 10 includes an anterior leaflet 11a, a posterior leaflet 11p, and a septal leaflet 11s, and an annulus 12. In some circumstances, the tricuspid valve 10 may undergo stenosis or anatomical changes that cause tricuspid regurgitation, such as instances in which the distance between the anterio-septal commissure and the anterio-posterior commissure of the native tricuspid valve increases with the progression of a diseased state due to dilation of the annulus 12 of the tricuspid valve 10.

Figure 3:
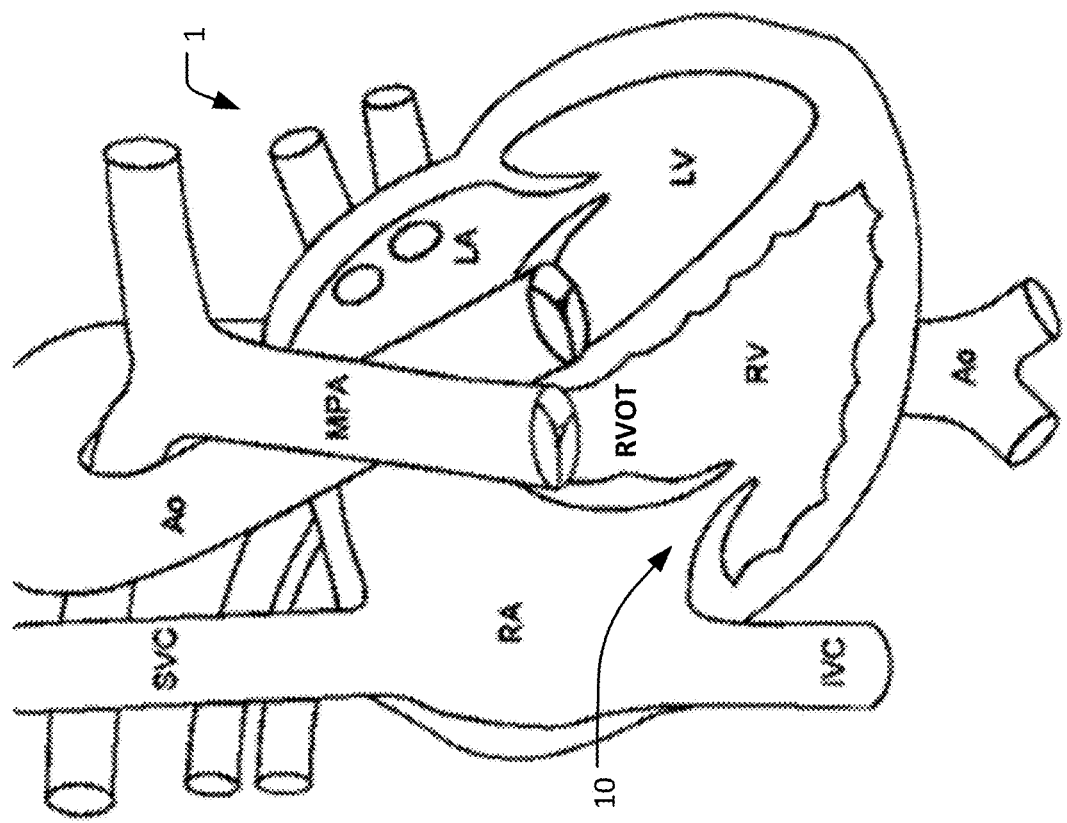
FIG. 3 shows another sectional view of a human heart including the four chambers (right atrium, right ventricle, left atrium, and left ventricle) and major conduits that deliver blood to the heart and transport blood away from the heart.

FIG. 3 illustrates a longitudinal sectional view of a human heart 1 that shows the four chambers (right atrium, right ventricle, left atrium, and left ventricle) and the major conduits that deliver blood to the heart 1 and transport blood away from the heart 1. The tricuspid valve 10 is located between the right atrium and the right ventricle. Blood enters the right atrium from the superior vena cava and the inferior vena cava. Blood flows from the right atrium to the right ventricle through the tricuspid valve 10. The blood exits the right ventricle and enters the main pulmonary artery ("MPA") via the RVOT that is adjacent to the tricuspid valve 10.

Figure 5:
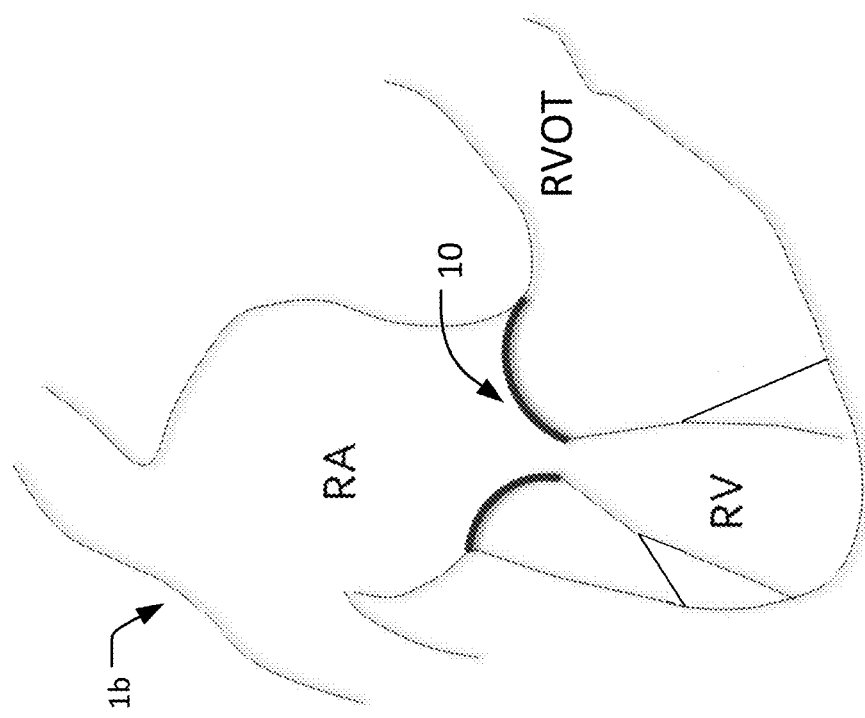
FIG. 5 shows another schematic view of the right side of the heart of FIG. 3, including the RA, RV, and RVOT, in accordance with some native anatomies.
Figure 4:
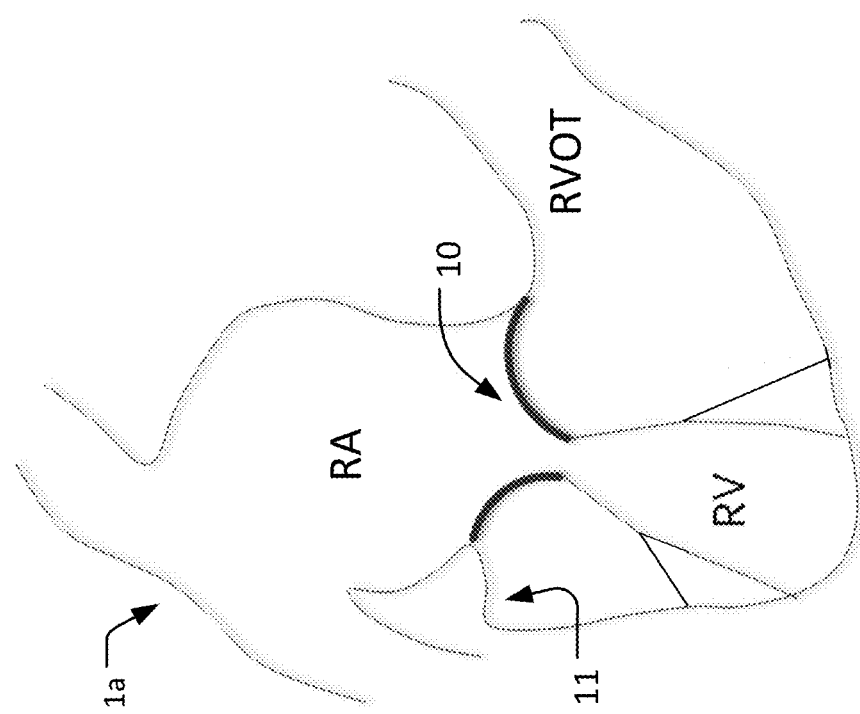
FIG. 4 shows a schematic view of the right side of the heart of FIG. 3, including the right atrium ("RA"), right ventricle ("RV"), and right ventricle outflow tract ("RVOT"), in accordance with some native anatomies.

FIGS. 4 and 5 schematically illustrate the right side of the heart 1, including the right atrium, right ventricle, and tricuspid valve 10 therebetween. Naturally, there is anatomical variability among the human population. FIGS. 4 and 5 depict some of the anatomical variability. In particular, FIG. 4 shows a heart 1a that includes the presence of a posterior shelf 11. In contrast, FIG. 5 shows a heart 1b with a lack of any such posterior shelf. Some human hearts (such as the heart 1a) have a posterior shelf 11, but some human hearts (such as the heart 1b) do not have a distinct posterior shelf. The prosthetic tricuspid valves disclosed herein are designed to be implantable in the native tricuspid valve 10 of both types of anatomies (e.g., both the heart 1a with the posterior shelf 11, and the heart 1b without the posterior shelf).

The posterior shelf 11, when present, provides an anatomical structure that can be used advantageously for the anchorage of a prosthetic tricuspid valve (as described further herein). When no such posterior shelf is present (e.g., as shown in FIG. 5), robust anchorage of a prosthetic tricuspid valve at the site of the native tricuspid valve 10 is more challenging. Nevertheless, and as described in U.S. patent application Ser. No. 17/747,507 filed on May 18, 2022) which is hereby incorporated by reference in its entirety and for all purposes), the prosthetic tricuspid valves described herein can be successfully used in such a case.

Figure 6:
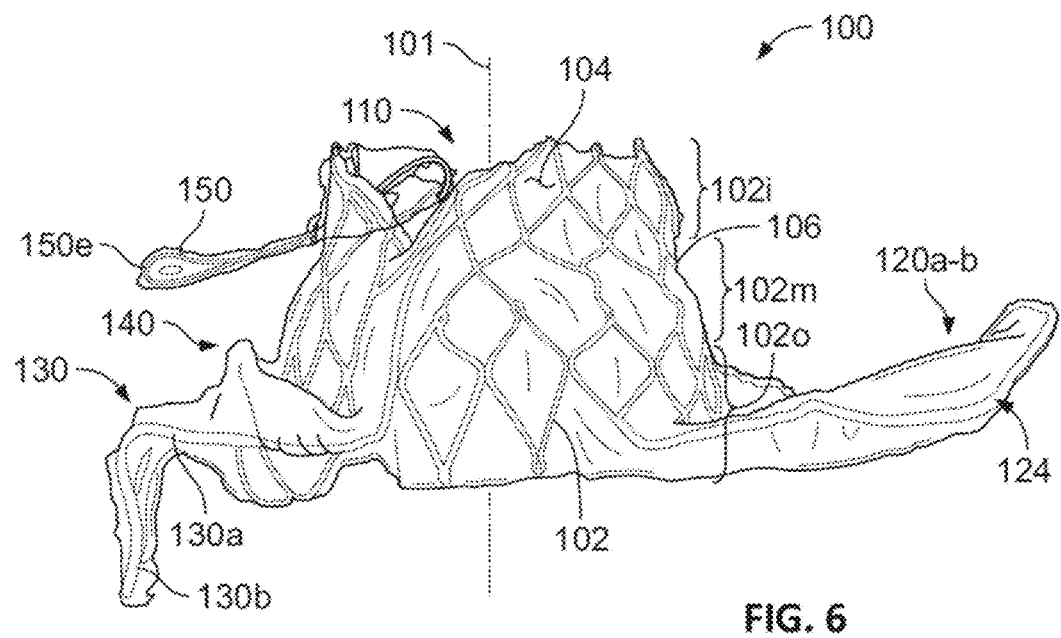
FIG. 6 shows a side view of an example prosthetic heart valve in accordance with some embodiments described herein.
Figure 7:
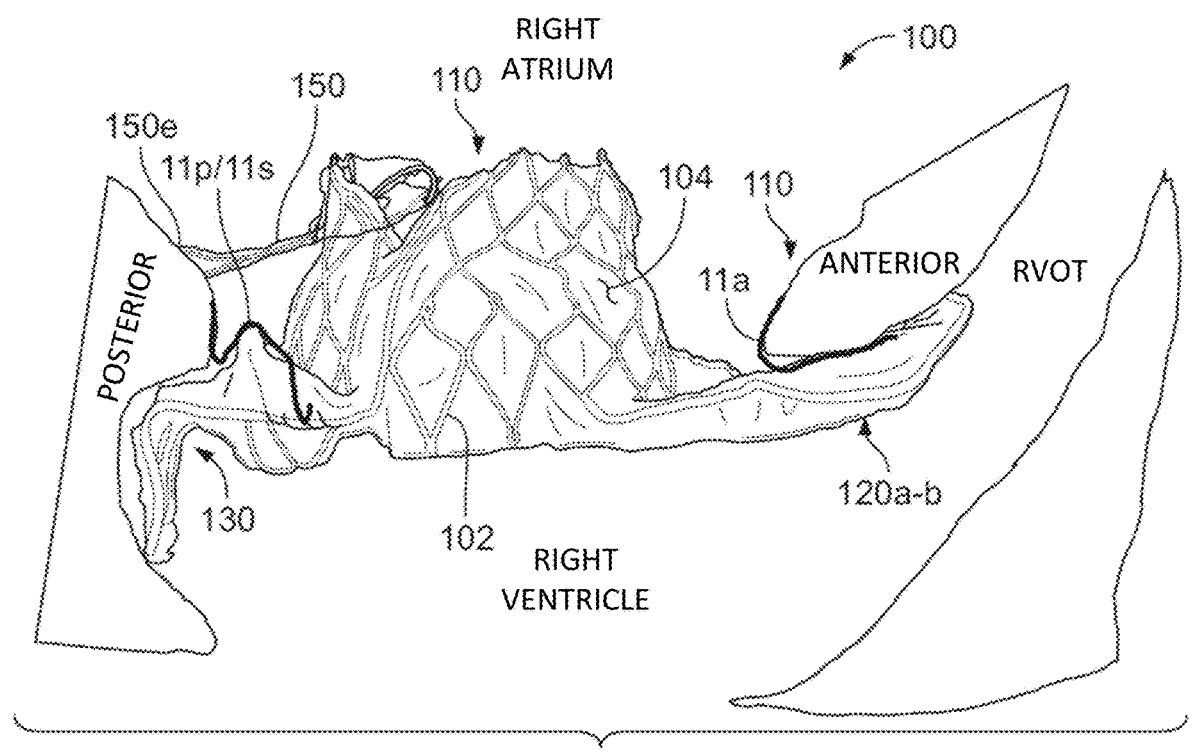
FIG. 7 shows a side view of the prosthetic heart valve of FIG. 6 engaged within a native tricuspid valve.
Figure 8:
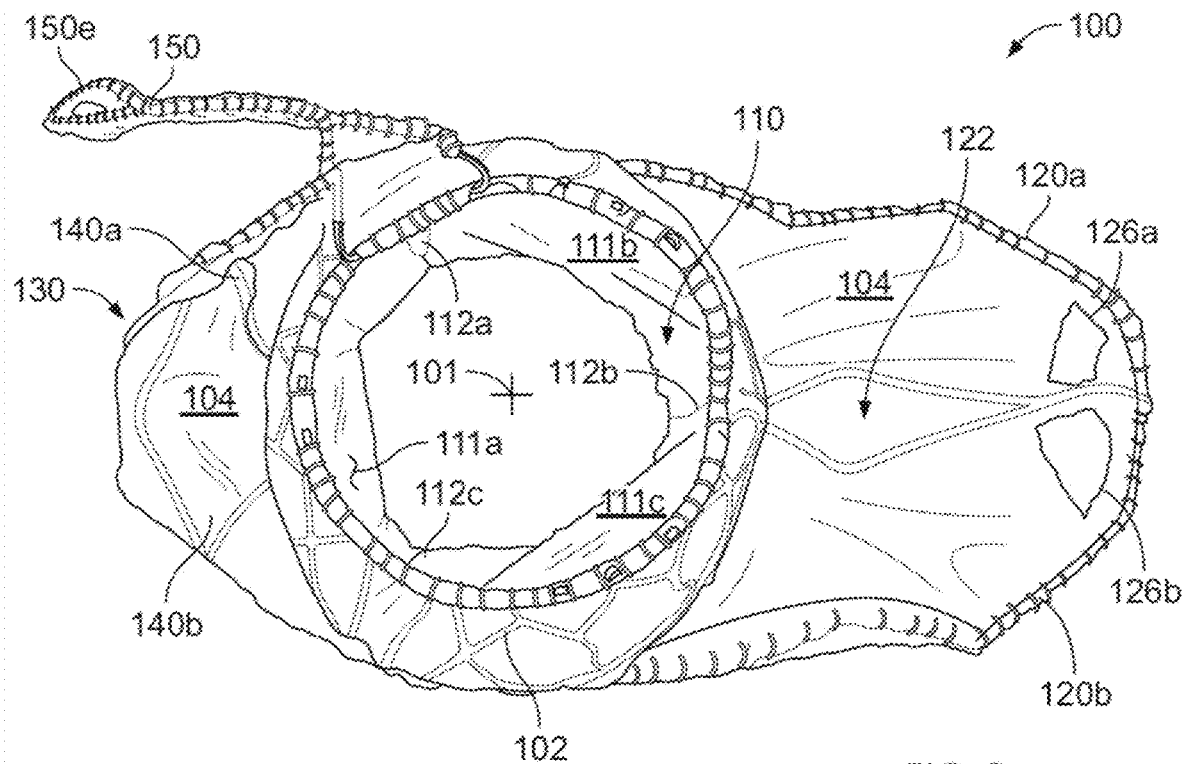
FIG. 8 shows a top view of the prosthetic heart valve of FIG. 6.

FIGS. 6-8 illustrate an example prosthetic tricuspid valve 100 (or simply "valve 100") in accordance with some example embodiments of this disclosure. The valve 100 includes a frame 102 and a covering 104 attached to the frame 102. FIG. 7 shows the valve 100 engaged with a native tricuspid valve 10 between the right atrium and the right ventricle.

The frame 102 comprises a cellular structure that provides mechanical support for the shape and structures of the valve 100. In some embodiments, the frame 102 is made from nitinol (NiTi), stainless steel, cobalt chromium, MP35N, titanium, polymeric materials, other biocompatible materials, or any combination thereof. Some or all parts of the frame 102 may be covered by the covering 104.

The frame 102 can be made of a laser cut, expanded, and shape-set material in some embodiments. The frame 102 is self-expanding in some embodiments. In some embodiments, the precursor material is tubular NiTi, a NiTi sheet, or other suitable types of precursor materials.

The covering 104 may made of a biocompatible polymer material (e.g., expanded polytetrafluoroethylene (ePTFE), UHMWPE (ultra-high molecular weight polyethylene), nylon, polyester (e.g., DACRON), or another synthetic material), natural tissues (e.g., bovine, porcine, ovine, or equine pericardium), or any combination thereof. The covering 104 can be attached to the frame 102 by suturing, using clips, adhesives, and/or any other suitable attachment process.

The valve 100 includes a main body 106. The main body 106 includes an occluder 110 (e.g., a one-way valve) that defines a central axis 101. The occluder 110 has flexible leaflets 111a, 111b, and 111c (collectively 111a-c) that cause the occluder 110 to function as a one-way valve (in a manner like a native tricuspid valve). The occluder 110 defines a circular inlet where the edges of leaflets 111a-c are attached to the frame 102. Other side edges of the leaflets 111a-c are attached to posts 112a, 112b, and 112c of the frame 102. The leaflets 111a-c also have distal free edges that are coaptable with each other to facilitate the opening and sealing of the occluder 110.

The main body 106 of the valve 100 includes an inflow end portion 102i, a mid-body portion 102m, and an outflow end portion 102o. The inflow end portion 102i includes a series of arch shapes in the frame 102, circumscribing the axis 101 of the occluder 110. The occluder leaflets 111a-c allow blood to directionally flow through the occluder 110 from the inflow end portion 102i to the outflow end portion 102o. The leaflets 111a-c of the occluder 110 close against each other (e.g., coapt) to prevent blood flow in the other direction (to prevent blood flow from the outflow end portion 102o to the inflow end portion 102i).

The embodiments of the valve 100 depicted in this disclosure employ three occluder leaflets 111a-c, which is referred to as tri-leaflet occluder. The occluder 110 of the valve 100 can optionally employ configurations other than a tri-leaflet occluder. For example, bi-leaflet, quad-leaflet, or mechanical valve constructs can be used in some embodiments. In particular implementations described herein, the flexible leaflets 111a-c are made of natural tissues such as porcine or bovine or equine or ovine pericardium. In such embodiments, the tissues are chemically cross-linked using glutaraldehyde or formaldehyde, or other aldehydes commonly used as crosslinking agents. In other embodiments, the flexible leaflets 111a-c are made of polymers such as polyurethane, polyester (DACRON) or expanded polytetrafluoroethylene (ePTFE). In some embodiments, the flexible leaflets 111a-c are attached to structural frame 102 using sutures that could be made of materials including but not limited to UHMWPE, nylon, or polyester (e.g., DACRON).

The valve 100 also includes a first anterior flap 120a (or septal anterior flap 120a), a second anterior flap 120b (or lateral anterior flap 120b), and at least one posterior flap 130. The frame 102 and the covering 104 combine to form the anterior flaps 120a-b and the posterior flap 130. The frame 102 provides the structure of the anterior flaps 120a-b and the posterior flap 130, and the covering 104 provides occlusion. While the depicted embodiment includes two anterior flaps 120a-b, in some embodiments one, three, four, or more than four anterior flaps can be included. While the depicted embodiment includes a single posterior flap 130, in some embodiments two, three, four, or more than four posterior flaps can be included. For instance, FIG. 31 refers to an embodiment with two posterior flaps 330a and 330b.

The anterior flaps 120a-b and the posterior flap 130 extend away from the outflow end portion 102o of the main body 106 in opposite directions away from the axis 101. That is, the posterior flap 130 extends directionally opposite from the extension direction of the first and second anterior flaps 120a-b. In some embodiments, the posterior flap 130 extends 180° opposite from the extension direction of the first and second anterior flaps 120a-b. In particular embodiments, the anterior flaps 120a-b and the posterior flap 130 extend away from the outflow end portion 102o of the main body 106 transverse to the axis 101 of the occluder 110.

In the depicted embodiment, the first anterior flap 120a and the second anterior flap 120b each include a mid-body portion 124 (FIG. 6) that is bent at an angle so as to direct terminal end portions of the anterior flaps 120a-b toward the inlet end of the main body 106. In some embodiments, the anterior flaps 120a-b initially extend away from the main body 106 substantially perpendicularly (e.g., within about 80° to 100°) to the central axis 101. Then, at the mid-body portion 124, the anterior flaps 120a-b have a bend that defines an angle θ in a range of between 20° to 60°, or 30° to 60°, or 30° to 70°, or 40° to 60°, or 40° to 70°, or 40° to 50°, without limitation.

The bends in the mid-body 106 of the anterior flaps 120a-b can allow the anterior flaps 120a-b to conform to the contours of the wall that defines the RVOT (as shown in FIG. 7). Accordingly, the bent anterior flaps 120a-b can reduce the potential of the anterior flaps 120a-b to restrict blood flow through the RVOT in some cases.

As shown in FIG. 8, the depicted embodiment includes an opening 126a that is defined by the covering 104 located at a terminal end portion of the first anterior flap 120a. Additionally, the covering 104 on the second anterior flap 120b defines an opening 126b at a terminal end portion of the second anterior flap 120b.

The openings 126a-b in the end portions of the anterior flaps 120a-b allow blood to flow through the anterior flaps 120a-b (via the openings 126a-b). This can be beneficial because in some implementations the anterior flaps 120a-b extend into the RVOT. Accordingly, such openings 126a-b may in some cases reduce the potential of the anterior flaps 120a-b to restrict blood flow through the RVOT.

In the depicted embodiment, the posterior flap 130 includes a first portion 130a and a second portion 130b that are arranged at an angle in relation to each other. The first portion 130a extends away from the outflow end portion 102o of the main body 106 generally transverse to the axis 101 of the occluder 110. The second portion 130b of the posterior flap 130 extends from the first portion 130a. In the depicted embodiment, the second portion 130b extends generally parallel to the axis 101 of the occluder 110. The angle defined between the first portion 130a and the second portion 130b can be in a range of 80° to 100°, or 70° to 110°, or 60° to 120°, or 50° to 130°, or 40° to 140°, without limitation.

The first anterior flap 120a and the second anterior flap 120b each extend in the same direction, which is opposite of the direction that the posterior flap 130 extends. In the depicted embodiment, portions of the first anterior flap 120a and the second anterior flap 120b overlap each other. An advantage of having the two separate anterior flaps 120a-b (rather than a single larger anterior flap) is that the anterior flap portion of the valve 100 can be radially compressed to a smaller profile for transcatheter delivery by the virtue of having the two separate anterior flaps 120a-b (as compared to having a single larger anterior flap).

In some embodiments, as shown in FIG. 7, the first and second anterior flaps 120a-b extend into the RVOT and overlap one axially on top of the other. This arrangement is functionally akin to a cantilevered beam arrangement. With the first and second anterior flaps 120a-b overlapping on each other, the bending resistance of the first and second anterior flaps 120a-b is increased (as compared to a single flap or non-overlapping flaps). This arrangement enables an advantageous extent of rigidity, without having to use framework members that are larger in cross-section. That is, the overlapping arrangement of the first and second anterior flaps 120a-b allow for the use of smaller framework members, which in turn importantly allows for a smaller collapsed delivery size (diameter). In other words, overlapping arrangement of the first and second anterior flaps 120a-b provides a support structure that is thicker without having to use a material with higher wall thickness (from which the framework is created); ultimately providing the bending stiffness or rigidity that keeps the valve 100 stable when RV pressure acts on the valve 100.

Figure 16:
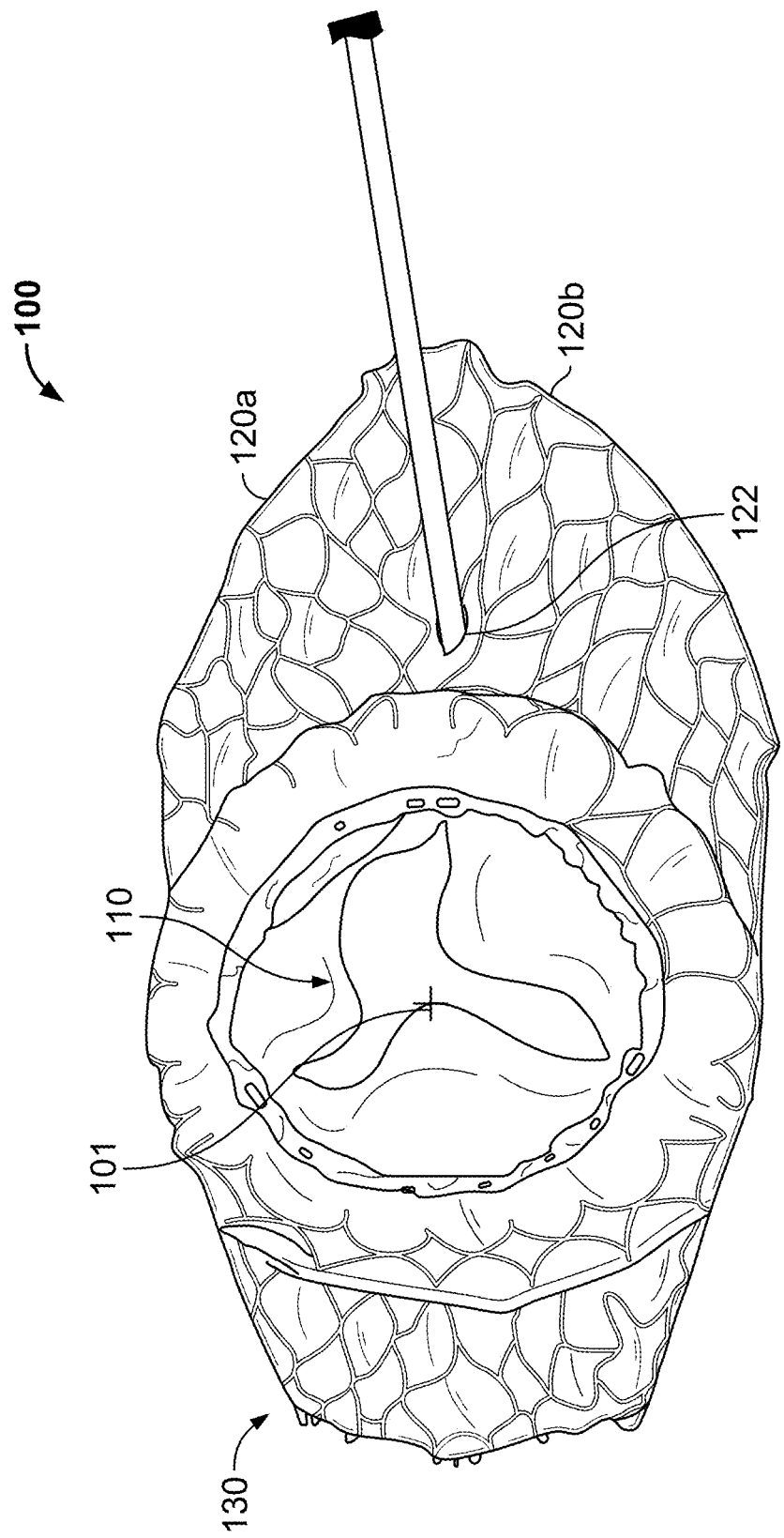
FIG. 16 shows a top view of some prosthetic heart valves described herein.

In the depicted embodiment, an open passage 122 (e.g., see FIG. 16) is defined between the first anterior flap 120a and the second anterior flap 120b. The open passage 122 can be used, for example, for passing a pacemaker lead through the valve 100, without disturbing the functioning of the occluder 110. Accordingly, the valve 100 can facilitate the pass-through of the pacemaker lead while still providing sealing to prevent tricuspid valve regurgitation from the RV to the RA. In some cases, the pacemaker lead is pre-existing and the valve 100 is implanted subsequently (with the open passage 122 being used to receive the pacemaker lead). In other cases, the valve 100 can be pre-existing and the pacemaker lead can be subsequently passed through the open passage 122. This could take place both during the same implant procedure, or as a subsequent procedure.

Figure 31:
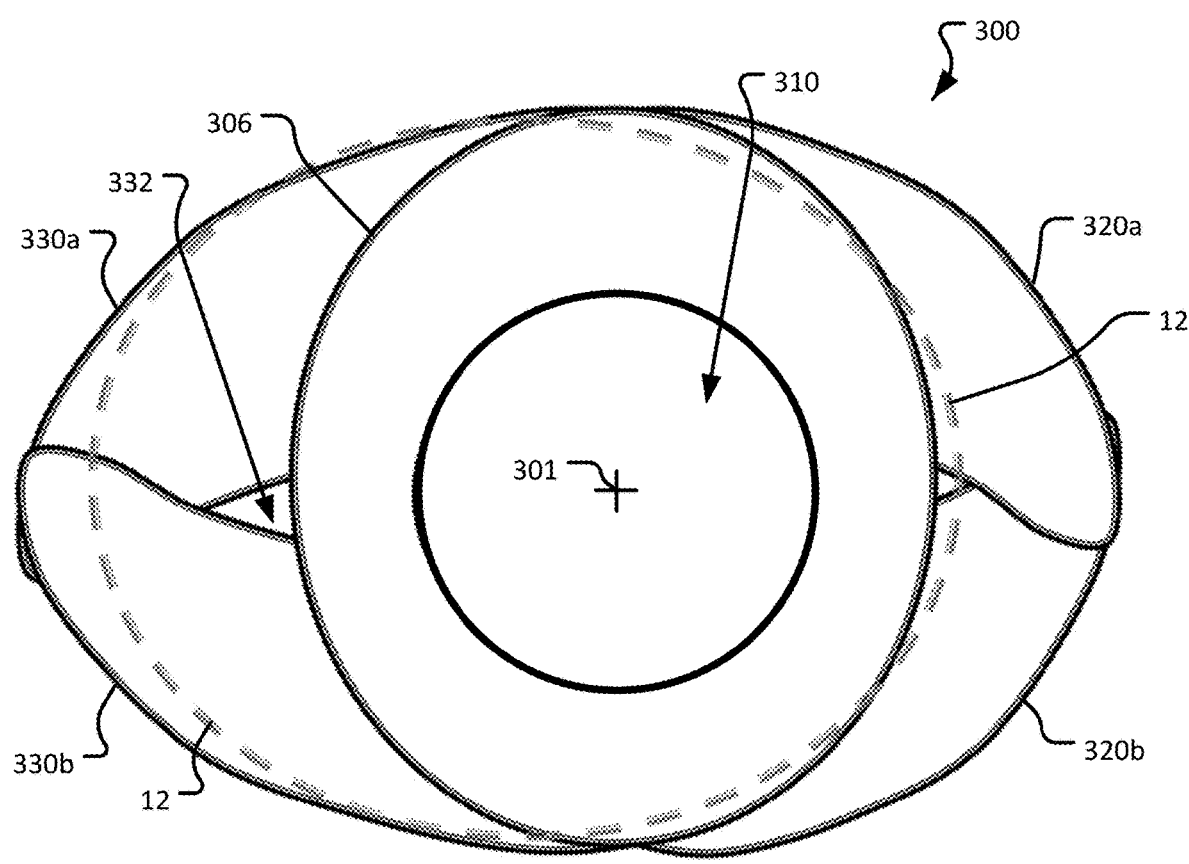
FIG. 31 schematically shows a top view of another example prosthetic heart valve in accordance with some embodiments described herein.

FIG. 31 illustrates another example prosthetic valve 300. The valve 300 defines an open passage 332 between the posterior flaps 330a and 330b that can be used, for example, for passing a pacemaker lead through the valve 300, without disturbing the functioning of the occluder 310. In some cases, the pacemaker lead is pre-existing and the valve 300 is implanted subsequently (with the open passage 322 being used to receive the pacemaker lead). In other cases, the valve 300 can be pre-existing and the pacemaker lead can be subsequently passed through the open passage 322.

Still referring to FIGS. 6-8, the valve 100 also includes one or more leaflet engagement members 140. In the depicted embodiment, the valve 100 includes two leaflet engagement members: a first leaflet engagement member 140a and a second engagement member 140b. In the depicted embodiment, the leaflet engagement members 140a-b extend from the outflow end portion 102o of the main body 106. In some embodiments, the leaflet engagement members 140a-b extend from the mid-body portion 102m of the main body 106.

The leaflet engagement members 140a-b extend from the frame 102 and bend toward the inflow end portion 102i of the main body 106. In other words, a portion of each leaflet engagement member 140a-b extends toward the inflow end portion 102i of the main body 106. A space, groove, or slot is defined between the leaflet engagement members 140a-b and the outer surface of the frame 102 (with the covering 104 being present on the frame 102 and leaflet engagement members 140a-b). As described further below, the space, groove, or slot receives and mechanically captures/holds a portion of a native leaflet (e.g., the posterior leaflet 11p and/or the septal leaflet 11s) to provide migration resistance for the valve 100.

In the depicted embodiment, the leaflet engagement members 140a-b extend from the frame 102 of the main body 106 in the same direction as the posterior flap 130. The posterior flap 130 extends away from the main body 106 farther than the leaflet engagement members 140a-b. Various other arrangements of the leaflet engagement members 140a-b and the posterior flap 130 are also envisioned and within the scope of this disclosure. The leaflet engagement members 140a-b may be U-shaped wire loops, as in the depicted embodiment. The wire loops that make up the leaflet engagement members 140a-b can be continuous with the wire members of the frame 102.

In the depicted embodiment, the leaflet engagement members 140a-b terminate at free ends. Accordingly, the leaflet engagement members 140a-b point toward the inflow end portion 102i of the main body 106, with the free ends of the leaflet engagement members 140a-b being the closest to the inflow end portion 102i. This arrangement defines the space, groove, or slot receives and mechanically captures/holds a portion of a native leaflet to provide migration resistance for the valve 100.

The depicted embodiment of the valve 100 includes an optional posterior arm 150. The posterior arm 150 comprises a wire member (e.g., an elongated loop) that extends from the frame 102 and includes a free end 150e (which can also be said to be located at a distal end portion of the posterior arm 150). In some embodiments, the posterior arm 150 is a wire member that is constructed unitarily with wire members of the frame 120. Hence, it can be said that the posterior arm 150 is a portion of the frame 120. In the depicted embodiment, the covering 104 is attached to the posterior arm 150, including the free end 150e.

In the depicted embodiment, the posterior arm 150 extends from the inflow end portion 102i of the frame 102. The posterior arm 150 extends in a direction that is the same as, or that is generally (e.g., +/−20°) parallel to, the direction in which the posterior flap 130 extends. In some embodiments, the posterior arm 150 extends from the mid-body portion 102m of the frame 102. The location of the free end 150e is within a transverse plane (e.g., taken perpendicular to the axis 101) that intersects the mid-body portion 102m of the frame 102 or the inflow end portion 102i of the frame 102.

The posterior arm 150 provides additional anchorage and migration resistance for the valve 100. As depicted in FIG. 7, the free end 150e of the posterior arm 150 abuts against an anatomical structure when the valve 100 is engaged in a native tricuspid valve 10. In some cases, the free end 150e of the posterior arm 150 abuts against an interior wall of an inferior vena cava, or coronary sinus, or the right atrium, or another anatomical structure. Where it abuts can be largely a function of the variable anatomy from patient to patient. The migration resistance provided by the posterior arm 150 can be particularly advantageous during diastole when the occluder 110 is open to allow blood flow from the right atrium to the right ventricle via the occluder 110.

Figure 9:
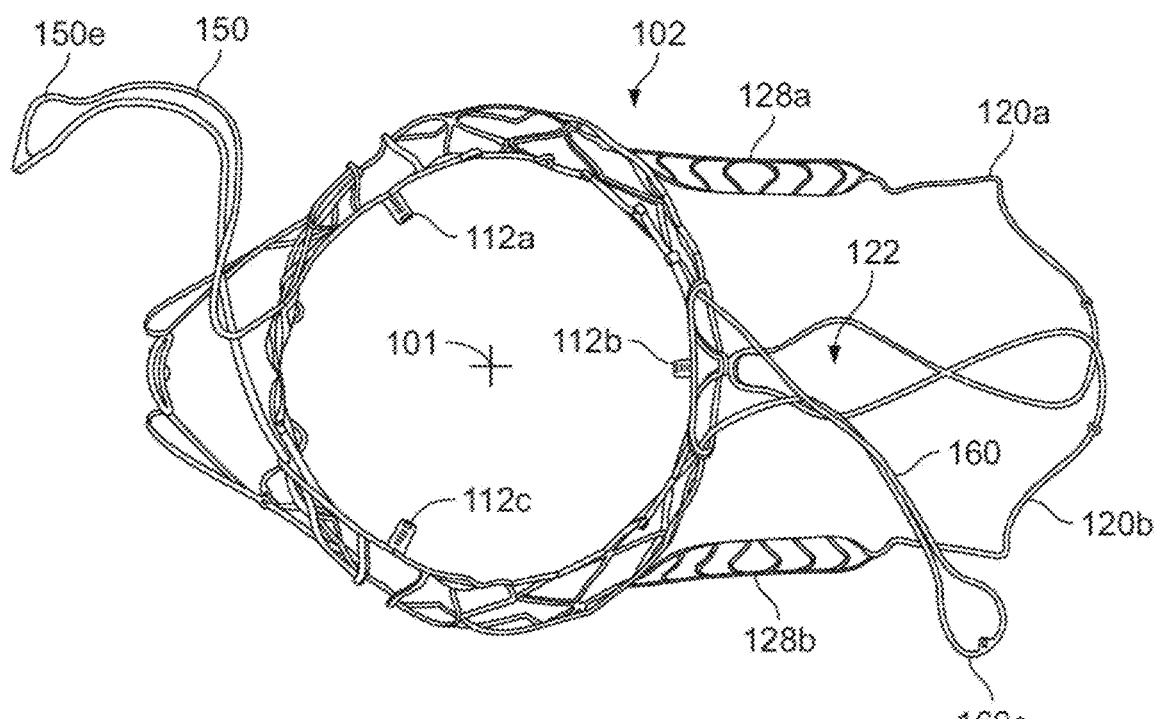
FIG. 9 shows a top view of a frame of another example prosthetic heart valve in accordance with some embodiments described herein.

Referring also to FIG. 9, in some embodiments the frame 102 can include an anterior arm 160. The anterior arm 160 may also be covered similarly to the posterior arm 150. The anterior arm 160 comprises a wire member (e.g., an elongated loop) that extends from the frame 102 and includes a free end 160e (which can also be said to be located at a distal end portion of the posterior arm 160). In some embodiments, the anterior arm 160 is a wire member that is constructed unitarily with wire members of the frame 120. Hence, it can be said that the anterior arm 160 is a portion of the frame 120. In the depicted embodiment, the covering 104 is attached to the anterior arm 160, including the free end 160e.

In the depicted embodiment, the anterior arm 160 extends from the inflow end portion 102i of the frame 102. The anterior arm 160 extends in an anterior direction away from the axis 101 (e.g., a direction that is generally the same as the direction in which the anterior flaps 120a-b extend). In some embodiments, the anterior arm 160 extends from the mid-body portion 102m of the frame 102. The location of the free end 160e is within a transverse plane (e.g., taken perpendicular to the axis 101) that intersects the mid-body portion 102m of the frame 102 or the inflow end portion 102i of the frame 102.

The anterior arm 160 provides additional anchorage and migration resistance for the valve 100. The free end 160e of the anterior arm 160 abuts against an anatomical structure when the valve 100 is engaged in a native tricuspid valve 10. In some cases, the free end 160e of the anterior arm 160 abuts against an interior wall of a right atrial appendage or another anatomical structure. Where the anterior arm 160 lands relative to the anatomy can vary based on patient to patient variability. The migration resistance provided by the anterior arm 160 can be particularly advantageous during diastole when the occluder 110 is open to allow blood flow from the right atrium to the right ventricle via the occluder 110.

Some embodiments of the valve 100 include the posterior arm 150, but not the anterior arm 160. Other embodiments of the valve 100 include the anterior arm 160, but not the posterior arm 150. Still other embodiments of the valve 100 include both the posterior arm 150 and the anterior arm 160.

Figure 10:
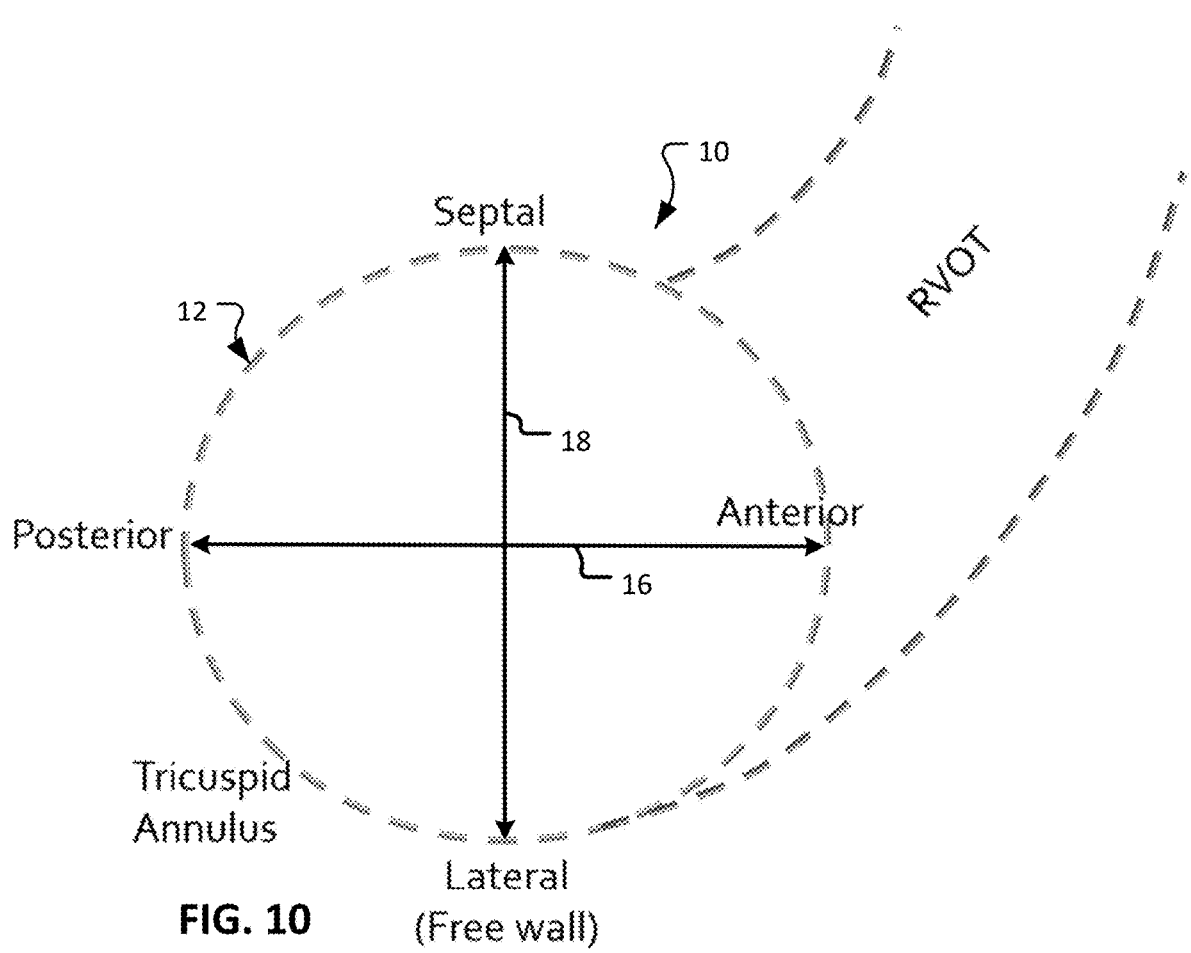
FIG. 10 schematically illustrates a transverse plane view of a native tricuspid valve annulus and RVOT.

FIG. 10 schematically illustrates a transverse plane view of a native tricuspid valve 10. The native tricuspid valve 10 includes the annulus 12. The RVOT extends away from the native tricuspid valve 10 along an arcuate path.

Figure 11:
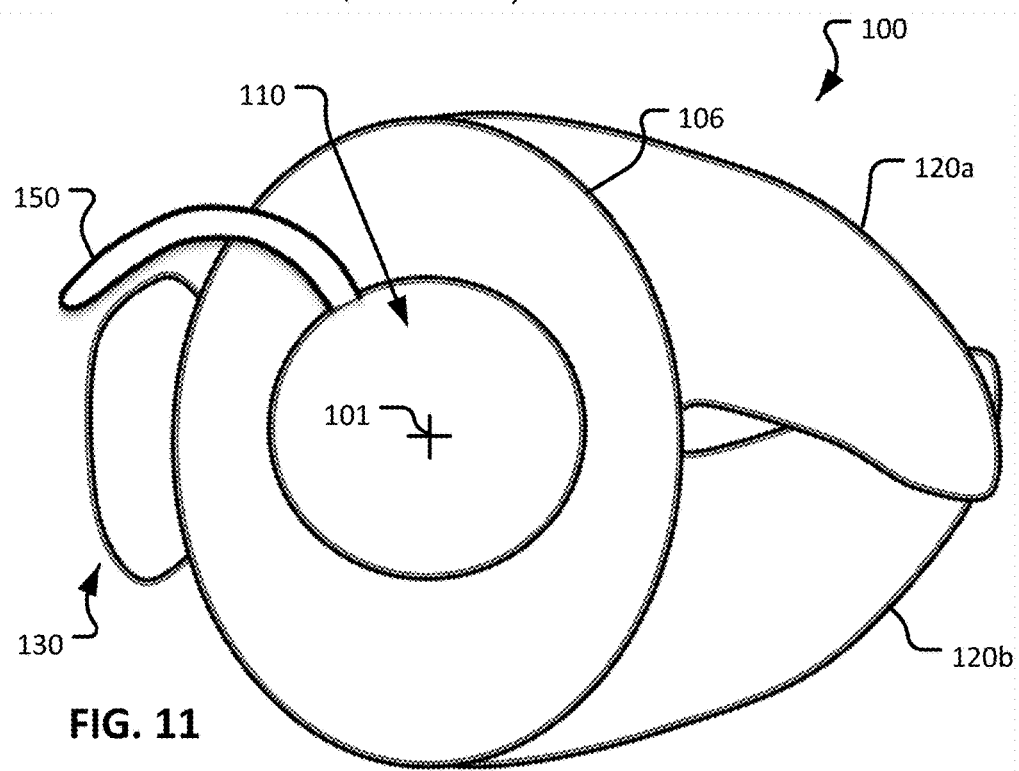
FIG. 11 schematically illustrates a top view of the prosthetic heart valve of FIG. 6.

FIG. 11 schematically illustrates a top view of the valve 100. The valve 100 includes the main body 106, the occluder 110, the septal anterior flap 120a, the lateral anterior flap 120b, the posterior flap 130, and the posterior arm 150.

Figure 12:
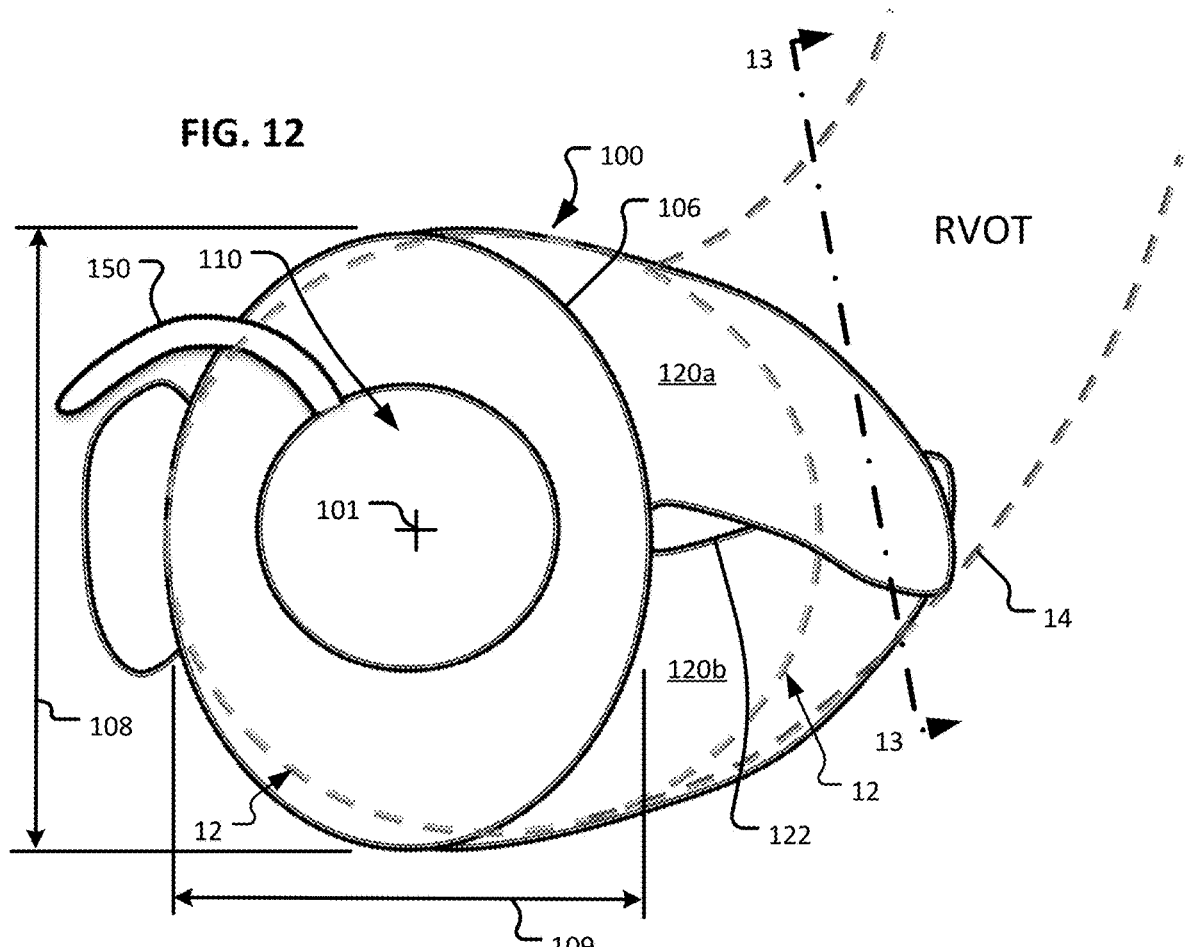
FIG. 12 schematically illustrates the prosthetic heart valve of FIG. 11 engaged with the native tricuspid valve annulus and RVOT of FIG. 10.

FIG. 12 schematically illustrates the valve 100 engaged in the anatomy of the native tricuspid valve 10 (that is also illustrated in FIG. 10). In this illustration, it can be seen how the septal anterior flap 120a and the lateral anterior flap 120b extend into the RVOT. Moreover, it can be seen that an edge of the lateral anterior flap 120b abuts against and extends along a lateral wall 14 of the RVOT.

Figure 13:
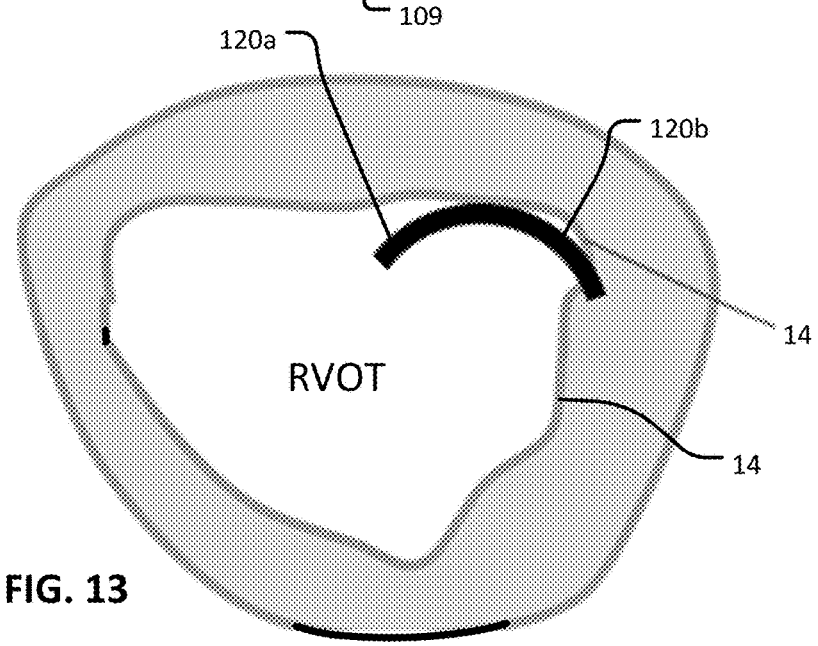
FIG. 13 schematically illustrates a cross-section view taken along the cutting plane 13-13 of FIG. 12 and including the anterior flaps of the prosthetic heart valve and the RVOT.

FIG. 13 schematically illustrates a cross-sectional view of the RVOT and distal end portions of the anterior flaps 120a-b. This cross-sectional view is taken along the cutting plane 13-13 shown in FIG. 12. It can be seen that the edge of the lateral anterior flap 120b abuts against and engages with the anatomical topography of the lateral wall 14 of the RVOT. The interfacing relationship between the lateral anterior flap 120b and the lateral wall 14 of the RVOT provides anchorage and migration resistance of the valve 100 relative to the native tricuspid valve 10. For example, there is a frictional migration resistance aspect provided by the normal forces exerted by the edge of the lateral anterior flap 120b against the lateral wall 14 of the RVOT. In addition, in some embodiments there is supplementary migration resistance provided because the edge of the lateral anterior flap 120b can seat against certain anatomical topographical features of the lateral wall 14 of the RVOT. In such a case, the lateral wall 14 physically supports the lateral anterior flap 120b and resists movement of the valve 10 relative to the anatomy of the native tricuspid valve 10 and RVOT. The interfacing relationship between the lateral anterior flap 120b and the lateral wall 14 of the RVOT provides anchorage and migration resistance of the valve 100 relative to the native tricuspid valve 10 that is particularly beneficial during diastole when the occluder 110 is open to allow blood flow from the right atrium to the right ventricle via the occluder 110.

Referring again to FIG. 10, the shape of the annulus 12 of many tricuspid valves is not circular. Often, as depicted here, shape of the annulus 12 is oblong or ovoidal (oval shaped). That is, the distance between the posterior and anterior regions of the annulus 12 is longer than the distance between the septal and lateral regions of the annulus 12. Accordingly, it can be said that the annulus 12 defines a major diameter 16 between the posterior and anterior regions, and a minor diameter 18 between the septal and lateral regions of the annulus 12.

Also referring again to FIG. 12, in this embodiment of the valve 100, the main body 106 has an ovular outer cross-sectional shape. In contrast, the occluder 110 within the main body 106 has a circular cross-sectional shape. The oval shaped main body 106 of the valve 100 has a major diameter 108 and a minor diameter 109. The anterior flaps 120a-b and the posterior flap 130 extend from the main body 106 along a direction that is transverse to the major diameter 108 of the oval shaped main body 106. In some embodiments, the anterior flaps 120a-b and/or the posterior flap 130 extend from the main body 106 substantially orthogonally or perpendicularly (e.g., 90°+/–5°, 90°+/–10°, 90°+/–15°, or 90° 30+/–20°) to the major diameter 108 of the oval shaped main body 106.

In some embodiments, as depicted in FIG. 12, the main body 106 is smaller than the full size/area of the annulus 12. Accordingly, the anterior flaps 120a-b can be used to fill up the internal area defined the annulus 12 that is not occupied by the main body 106. The occluder 110 occupies a circular cross-sectional area that is smaller than the cross-sectional area main body 106, which is adequate for the hemodynamics of the blood flow between the atrium and the ventricle. In some embodiments, the percentage of the internal area defined by the annulus 12 that is occupied by the main body 106 is about 50% (with the remaining about 50% of the area of the annulus 12 being covered by the anterior flaps 120a-b). In some embodiments, the percentage of the area of the annulus 12 that is occupied by the main body 106 is in a range of about 50% to 60%, or 55% to 65%, or 60%, to 70%, or 65% to 75%, or 70% to 80%, or 75% to 85%, or 60% to 80%, without limitation, with the anterior flaps 120a-b covering the remainder of the area of the annulus 12. In some embodiments, the anterior flaps 120a-b cover at least 50%, or at least 40%, or at least 30%, or at least 20%, or at least 10%, or at least 5% of the internal area defined by the annulus 12.

The fact that the anterior flaps 120a-b cover at least a portion of the area defined within the annulus 12 can be beneficial for additional reasons. For example, if, at some point in the future after the valve 100 has been implanted in the annulus 12, a pacemaker lead needs to be passed through the annulus 12, then a location on the anterior flaps 120a-b can be punctured to allow the pacemaker lead to pass through the anterior flaps 120a-b. The puncture can be at the open passage 122, or at another location of the anterior flaps 120a-b. The ability to pass a pacemaker lead through the anterior flaps 120a-b is advantageous because doing so does not affect the functionality of the occluder 110. This is advantage is made possible by the fact that the anterior flaps 120a-b cover at least a portion of the area of the annulus 12.

Since, as depicted in the example of FIG. 12, in some cases a portion of the oval shaped annulus 12 is covered by the anterior flaps 120a-b, the main body 106 need not be circular, and can be constructed to have various types of cross-sectional shapes. An oval shape (as shown) may be preferable in some cases, as it can be radially compressed well for fitting in a low-profile delivery catheter because it can have a smaller perimeter due to the minor diameter 109 of the main body 106 being shorter than the major diameter 108. If, for example, the main body 106 had a circular cross-sectional shape with a diameter equal to the major diameter 108, the main body 106 could not be radially crushed/compressed to as small of a size as the depicted oval shaped main body 106. Hence, a larger delivery sheath would be required if the main body 106 was circular (as compared to ovular as shown).

Interestingly, in the example depicted in FIG. 12, while both the annulus 12 of the tricuspid valve 10 and the main body 106 of the valve 100 are oblong or oval shaped, the orientations of their major and minor diameters are about 90° (e.g., 90°+/–10°) offset in relation to each other when the valve 100 is implanted in the tricuspid valve 10. That is, the major diameter 108 of the oval shaped main body 106 is substantially parallel (e.g., +/–10°) relative to the minor diameter 18 of the annulus 12. Moreover, the minor diameter 109 of the oval shaped main body 106 is substantially parallel (e.g., +/–10°) relative to the major diameter 16 of the annulus 12. These geometric relationships are beneficial because the annulus 12 is fully occluded by the valve 100 and the diameter of the radially compressed delivery configuration of the valve 100 can be reduced (as compared to having the main body 106 filling a larger area of the annulus 12).

Again, it is evident in FIG. 12 that the opening defined by the native annulus 12 is not completely filled by the main body 106. Instead, the laterally-extending first and second anterior flaps 120a-b help to cover and fluidly seal the native tricuspid valve opening which is not circular in this example (e.g., with the native valve opening being oblong, or irregularly shaped). In other words, in combination with the main body 106 of the valve 100, the first and second anterior flaps 120a-b (and the laterally-extending posterior anchoring flap 130 in some cases) help to cover and fluidly seal the native tricuspid valve opening which is not circular in some cases. In addition, terminal end portions of the first and second anterior flaps 120a-b extend into the RVOT to provide anchoring and migration resistance. Accordingly, the first and second anterior flaps 120a-b perform both sealing and anchorage.

In some cases, the shape of a patient's native annulus 12 is generally circular. In such a case, the valve 100 can still provide much of the benefits described above. For example, the main body 106 can still have an oblong or oval-shaped outer cross-sectional shape that occupies less than the full circular area of the native annulus 12 (with the first and second anterior flaps 120a-b occupying the remainder). In that case, the valve 100 is implanted in the native annulus 12 such that the central axis 101 of the occluder 110 is laterally offset (e.g., in the posterior direction) from the geometric center of the generally circular native annulus 12. In addition, the major diameter 108 of the main body 106 can be shorter than the diameter of the native annulus 12. For example, in some embodiments the length of the major diameter 108 of the main body 106 is about 60% to 80% of the diameter of the native annulus 12, or about 70% to 90% of the diameter of the native annulus 12, or about 80% to 95% of the diameter of the native annulus 12, without limitation.

Figure 14:
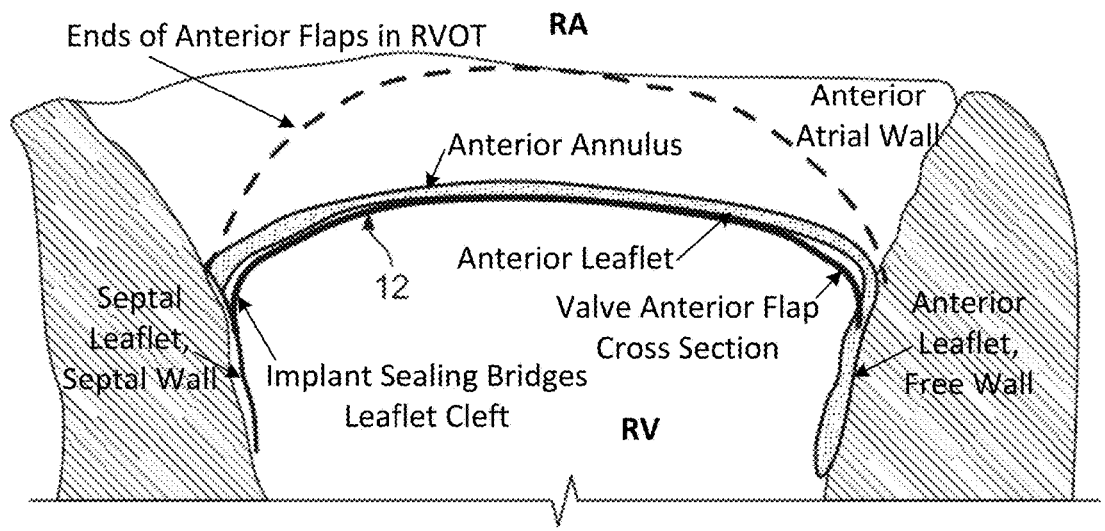
FIG. 14 schematically shows a longitudinal plane cross-section view of an anterior portion of a native tricuspid valve annulus and the anterior flaps of prosthetic heart valves described herein.

FIG. 14 illustrates a longitudinal plane cross-section view (e.g., approximately parallel to the central axis of the annulus 12) near an anterior portion of the native tricuspid valve annulus 12. This view is from the interface between the RVOT and the native tricuspid valve annulus 12, looking toward the right atrium and right ventricle. In this view, it can be seen that the anterior annulus 12 is curved.

Figure 15:
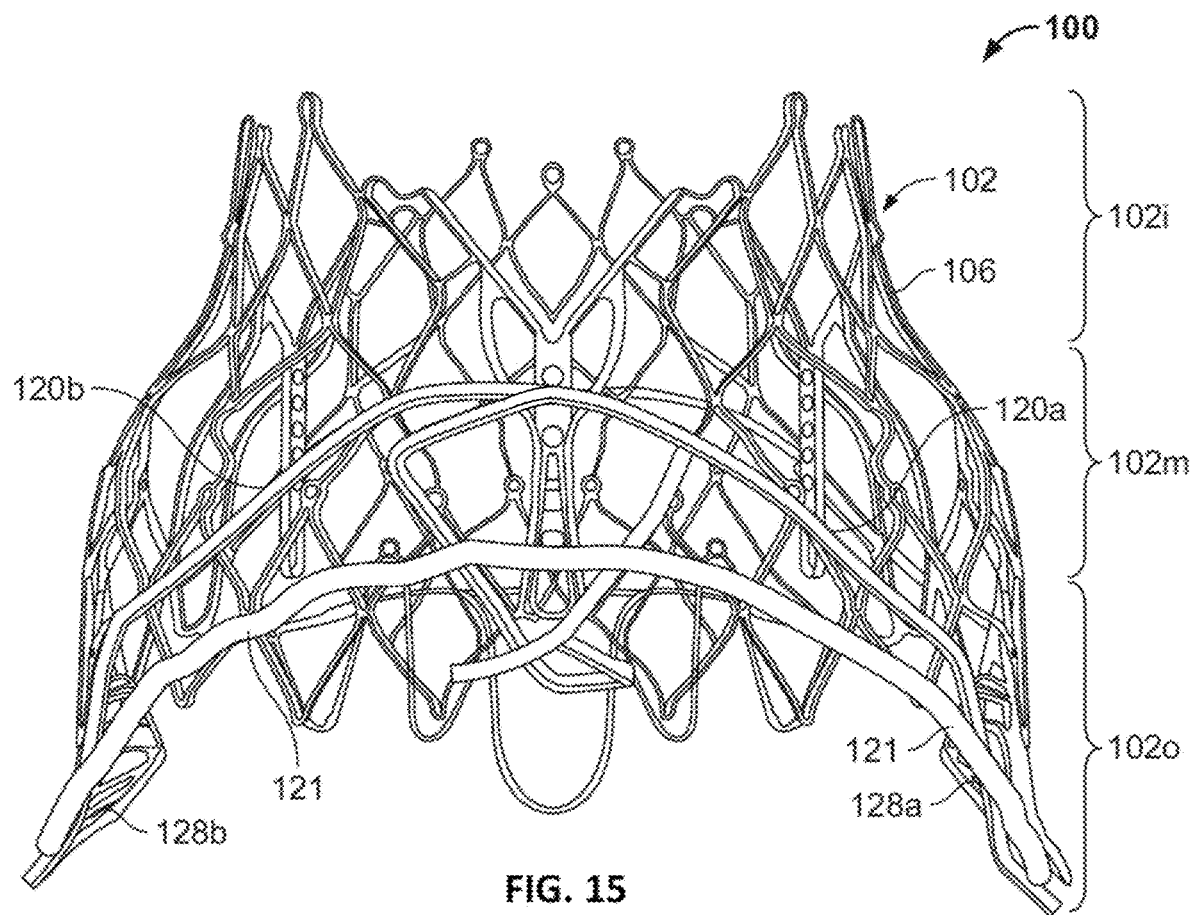
FIG. 15 is an anterior side view of the prosthetic heart valves described herein showing a cross-sectional shape of the anterior flaps.

FIG. 15 shows an anterior end view of the frame 102 of the valve 100 (without the covering 104 in this example). The first and second anterior flaps 120a-b are in the foreground in this view, and the main body 106 is in the background.

A heavy line 121 has been superimposed on FIG. 15 to represent the cross-sectional shape of the first and second anterior flaps 120a-b (when the covering 104 is attached to the frame 102). It can be seen that the cross-sectional shape of the first and second anterior flaps 120a-b (taken perpendicularly to the direction in which the first and second anterior flaps 120a-b extend from the main body 106) is curved or arcuate. The arc extends from the outflow end portion 102o of the frame 102 toward the inflow end portion 102i, with the middle of the arc being the closest point of the arc to the inflow end portion 102i.

The curved or arcuate cross-sectional shape of the first and second anterior flaps 120a-b is beneficial because, as described in reference to FIG. 14, the anterior portion of the native tricuspid valve annulus 12 with which the first and second anterior flaps 120a-b interface is also curved. Accordingly, a good sealing interface between the arced first and second anterior flaps 120a-b and the arced anterior portion of the native tricuspid valve annulus 12 is created by these complimentary curved shapes. This sealing arrangement between the arced first and second anterior flaps 120a-b and the native tricuspid valve annulus 12 can be beneficial for mitigating paravalvular leaks when the valve 100 is engaged with the native tricuspid valve 10.

As shown in FIG. 15, in the depicted embodiment the arcuate cross-sectional shape of the first and second anterior flaps 120a-b is at least partially facilitated by the configuration of frame portions 128a and 128b (also visible in FIG. 9). The frame portions 128a and 128b constitute interior parts of the outer edges of the first and second anterior flaps 120a-b. The frame portions 128a and 128b are arranged at a non-zero angle in relation to the central axis 101 so as to help define the arcuate cross-sectional shape of the first and second anterior flaps 120a-b that is represented by the heavy line 121. In some embodiments, the angle between the frame portions 128a and 128b and the central axis 101 is between 20° to 50°, or between 30° to 60°, or between 40° to 70°, without limitation. The frame portions 128a and 128b near the outer edges of the first and second anterior flaps 120a-b perform particularly advantageously to create good seals between the first and second anterior flaps 120a-b and the anterior portion of the native tricuspid valve annulus 12, because paravalvular leaks are particularly prone to occur in those edge areas.

FIGS. 17 and 18 illustrate an example prosthetic heart valve deployment system 200 (or simply "deployment system 200"). The deployment system 200 includes a control handle 210, an outer sheath catheter 220, a middle deflectable catheter 230, and an inner control catheter 240. The outer sheath catheter 220 defines a first lumen. The middle deflectable catheter 230 is slidably disposed in the first lumen and defines a second lumen. The inner control catheter 240 is slidably disposed in the second lumen.

The inner control catheter 240 includes a curved portion 242. The curved portion 242 is elastically deformable. That is, while the curved portion 242 is located within the confines of the first lumen of the outer sheath catheter 220, the curved portion 242 is essentially linear (or at least more linear than when the curved portion 242 is radially unconstrained). When the curved portion 242 of the inner control catheter 240 is distally expressed out (either by pushing the inner control catheter 240 distally or by pulling the outer sheath catheter 220 proximally) from the confines of the first lumen of the outer sheath catheter 220, the curved portion 242 then naturally elastically reconfigures to exhibit a pronounced curve (e.g., as shown in FIG. 18). Thus, it can be said that the natural shape of the inner control catheter 240 includes the curved portion 242 that defines an interior angle 9. In some embodiments, the interior angle 9 can be between 130° and 160°, or between 120° and 150°, or between 110° and 140°, or between 100° and 130°, or between 90° and 120°, or between 80° and 110°, or between 80° and 100°, without limitation. In some embodiments, the interior angle θ can be less than 160°, or less than 150°, or less than 140°, or less than 135°, or less than 130°, or less than 120°, or less than 110°, or less than 100°, or less than 90° without limitation.

The middle deflectable catheter 230 includes a selectively deflectable distal end portion 232 with at least one plane of deflection. In some embodiments, the selectively deflectable distal end portion 232 is deflectable in two planes. In some embodiments, the middle deflectable catheter 230 includes two or more separate selectively deflectable portions that are in same planes or in different planes.

In the depicted embodiment, the selectively deflectable distal end portion 232 is deflectable in a same plane as the plane of the curved portion 242 of the inner control catheter 240. Accordingly, when the selectively deflectable distal end portion 232 of the middle deflectable catheter 230 is deflected, the curvature of the combination of the middle deflectable catheter 230 and the inner control catheter 240 in relation to the axis of the outer sheath catheter 220 is increased beyond that of the interior angle θ alone. In some embodiments, the combined curvature of the middle deflectable catheter 230 and the inner control catheter 240 in relation to the axis of the outer sheath catheter 220 can define an interior angle between 90° and 110°, or between 80° and 100°, or between 700 and 90°, or between 60° and 80°, or between 50° and 70°, or between 30° and 60°, or between 0° and 30°, without limitation. This high degree of curvature can be beneficial during deployment of a prosthetic valve (such as the valve 100) using the deployment system 200, as described further below.

The inner control catheter 240 can also include mechanical features for releasably coupling with a prosthetic valve (such as the valve 100). For example, in the depicted embodiment, the inner control catheter 240 includes one or more control wires and/or release pins 244 that can releasably couple the valve 100 to the inner control catheter 240 in a low profile delivery configuration.

Figure 20:
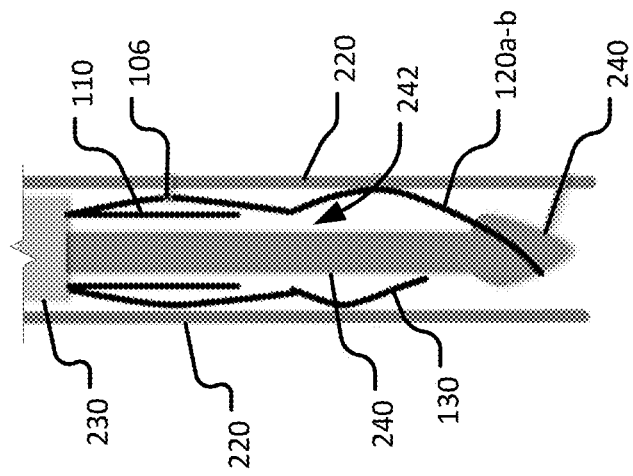
FIG. 20 schematically shows the prosthetic tricuspid valve of FIG. 19 coupled with the prosthetic heart valve deployment system of FIG. 17.
Figure 19:
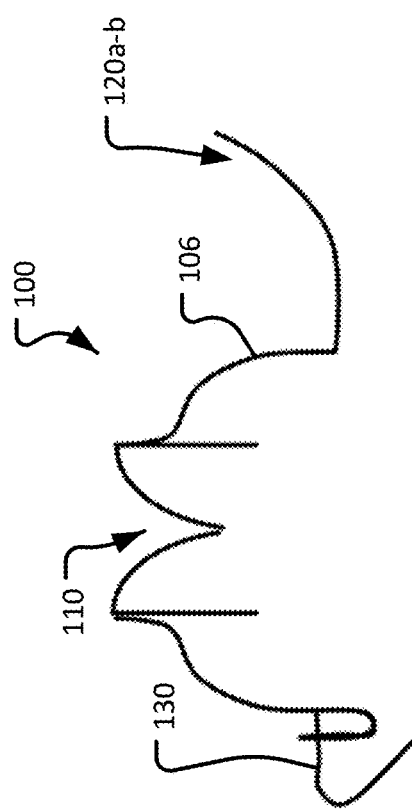
FIG. 19 schematically illustrates a side view of the prosthetic tricuspid valves described herein.

FIG. 19 shows a schematic illustration of the valve 100. FIG. 20 schematically shows the valve 100 coupled to the inner control catheter 240 and located within the first lumen defined by the outer sheath catheter 220. The distal tip of the middle deflectable catheter 230 is also visible. In this arrangement, the valve 100 is radially compressed to a low-profile delivery configuration while within the outer sheath catheter 220. In some embodiments, the valve 100 (or portions thereof are wrapped or folded around the inner control catheter 240. For example, in some embodiments the anterior flaps 120a-b are wrapped around the inner control catheter 240. The valve 100 can self-expand as its emergence from the outer sheath catheter 220 takes place (e.g., by the manual retraction of the outer sheath catheter 220 relative to the middle deflectable catheter 230 and the inner control catheter 240).

In some embodiments, when the valve 100 is in its collapsed delivery configuration within the outer sheath catheter 220, the portions of the valve 100 are arranged relative to each other as follows. The first and second anterior flaps 120a-b (which can be wrapped on each other) are distal-most. The occluder portion (or valve core) 110 with the flexible leaflets is proximal-most within the outer sheath catheter 220. The posterior anchoring flap 130 is arranged between the distal-most first and second anterior flaps 120a-b and the proximal-most occluder portion 110.

The valve 100 can be releasably coupled to the inner control catheter 240 using the one or more control wires and/or release pins 244 (FIG. 18). In some embodiments, a first control wire is releasably coupled to a proximal end portion of the main body 106, a second control wire is releasably coupled to a distal end portion of the main body 106, and a third control wire is releasably coupled to the posterior flaps 120a-b. The control wires can be tensioned to draw and maintain the associated portion of the valve 100 radially inward to be snug against the inner control catheter 240. During deployment of the valve 100, the control wires can be individually relaxed to allow the associated portion of the valve 100 to expand elastically toward its natural expanded shape.

Still referring to FIG. 20, in this delivery configuration the curved portion 242 of the inner control catheter 240 is being constrained in an essentially linear configuration by the outer sheath catheter 220. However, when the inner control catheter 240 is expressed from the outer sheath catheter 220 (or as the outer sheath catheter 220 is pulled proximally relative to the inner control catheter 240), the curved portion 242 will become unconstrained and will elastically deflect to its natural curved configuration (e.g., as shown in FIG. 18). The curved configuration of the curved portion 242 is beneficial for the deployment process of the valve 100 into engagement with a native tricuspid valve 10, as described further below.

FIGS. 21-30 illustrate a series of steps for deploying a prosthetic heart valve (such as the heart valve 100 described herein in any of its variations) using the heart valve deployment system 200. These figures illustrate a trans-jugular vein approach to the native tricuspid valve 10 (via the superior vena cava).

Figure 21:
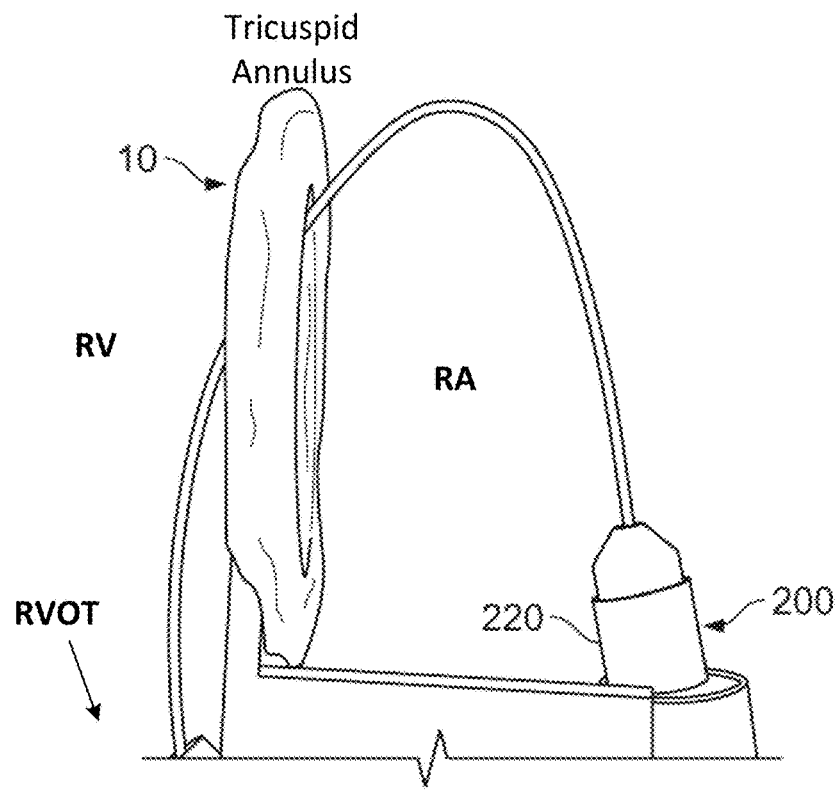
FIGS. 21 through 30 show an example trans-jugular method of deploying the prosthetic tricuspid valves described herein using the prosthetic heart valve deployment system of FIG. 17.

FIG. 21 shows a distal end portion of the deployment system 200 emerging into the right atrium via the superior vena cava. The deployment system 200 is being advanced over a guidewire that was installed previously. The valve 100 (not visible) is within the outer sheath catheter 220.

Figure 22:
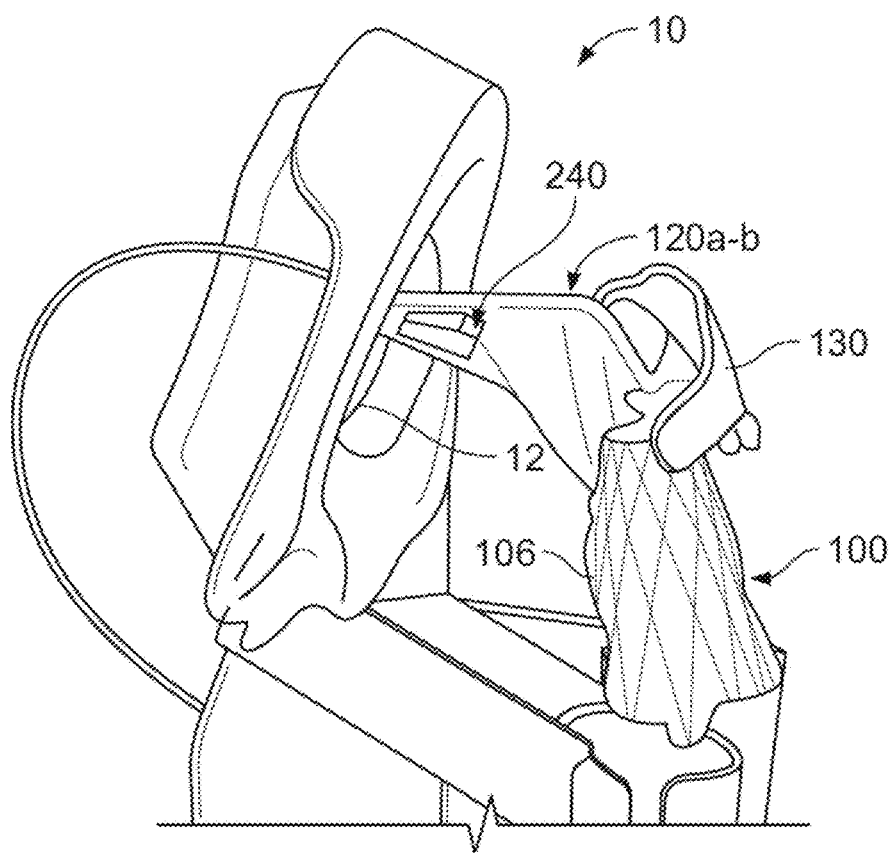

FIG. 22 illustrates the valve 100 (while the valve 100 is releasably coupled to the inner control catheter 240) after the withdrawal of the outer sheath catheter 220 and/or the advancement of the inner control catheter 240 and the middle deflectable catheter 230. At this stage, the curved portion 242 (not visible under the valve 100) has become unconstrained and has elastically deflected to its natural curved configuration. The natural curved configuration of the curved portion 242 facilitates the inner control catheter 240 to make a relatively tight turn within the right atrium to advance from the vena cava and through the annulus 12 of the native tricuspid valve 10 as depicted.

Figure 23:
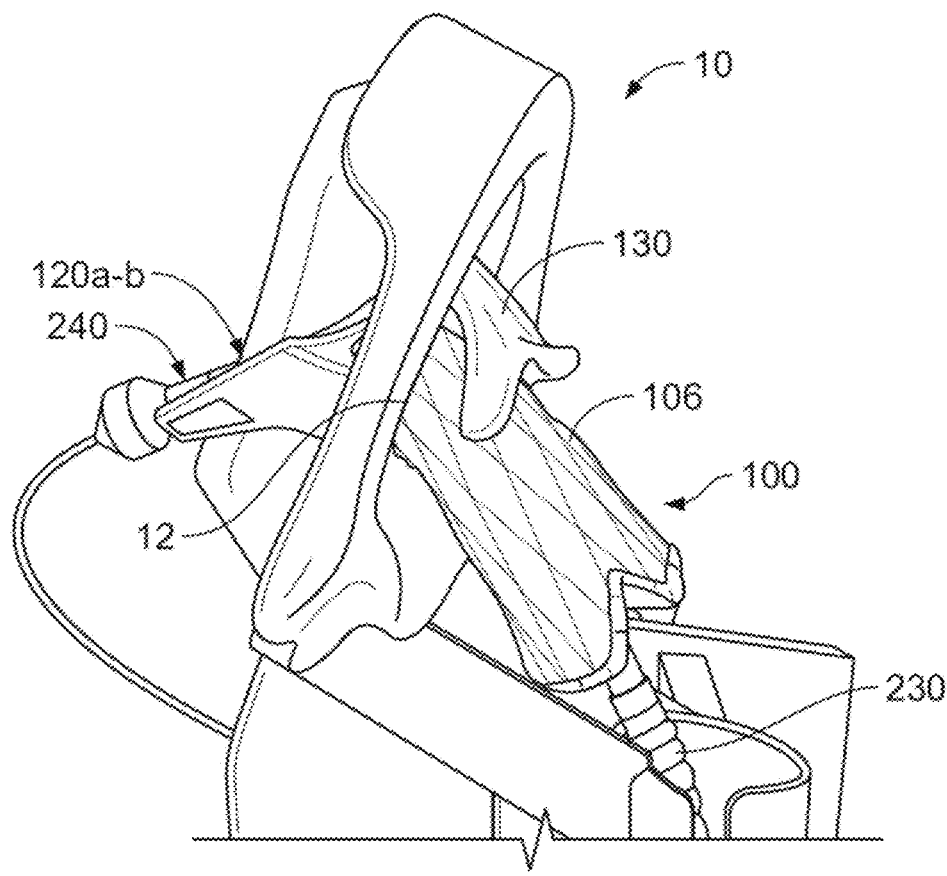
Figure 24:
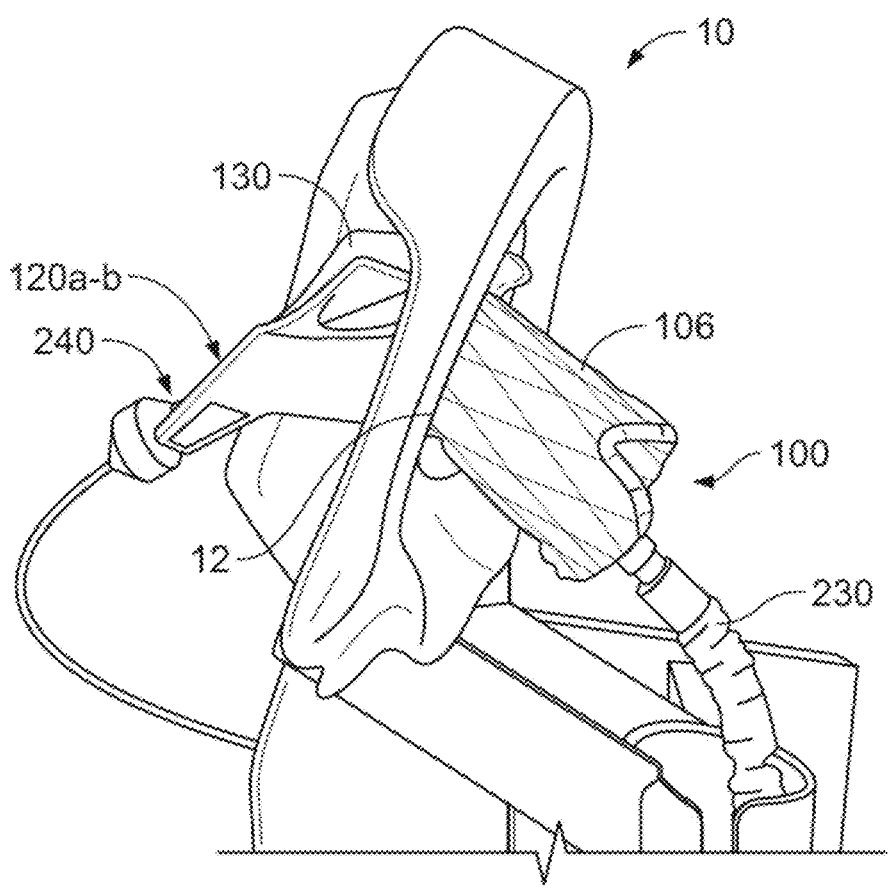

FIGS. 23 and 24 illustrate further advancement of the valve 100 (while the valve 100 is still releasably coupled to the inner control catheter 240). In these images, the middle deflectable catheter 230 is being deflected (by a first amount in FIG. 23 and a greater amount in FIG. 24). The deflection of the middle deflectable catheter 230 adds to the curvature of the inner control catheter 240 to enable the distal end portion of the inner control catheter 240 to become directed toward the RVOT after passing through the annulus 12 (as shown in FIG. 24).

Figure 25:
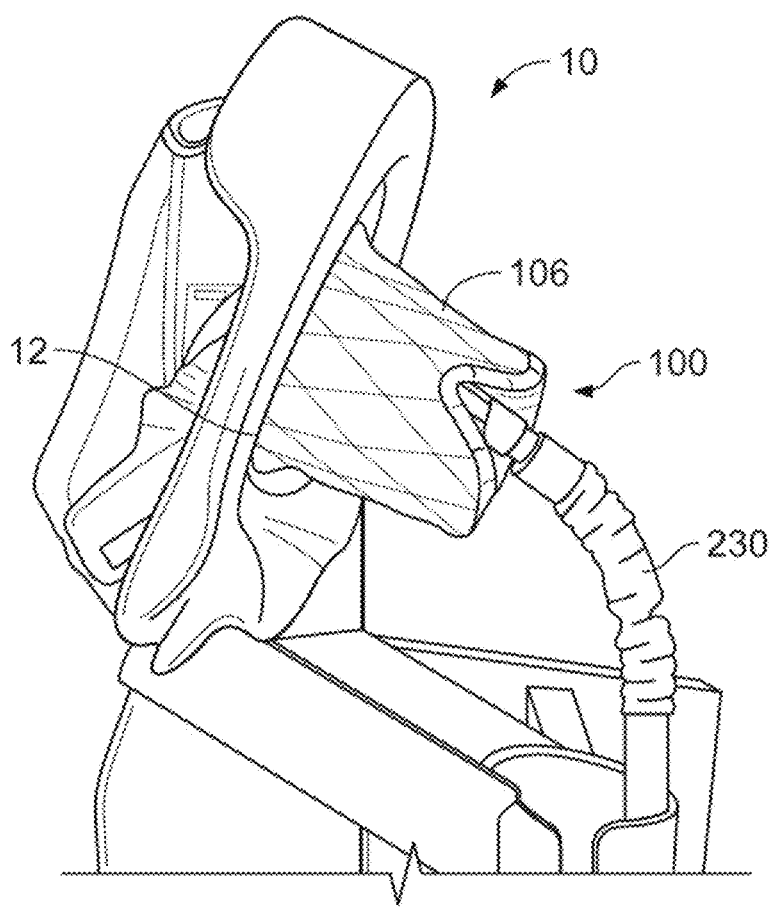
Figure 26:
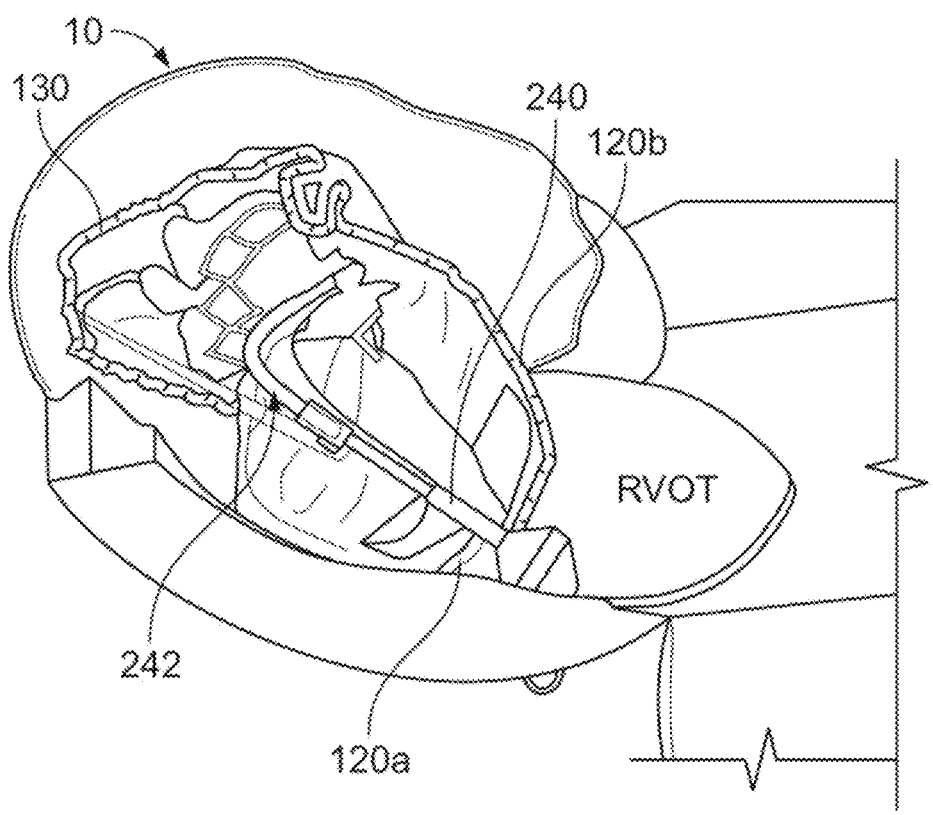
Figure 27:
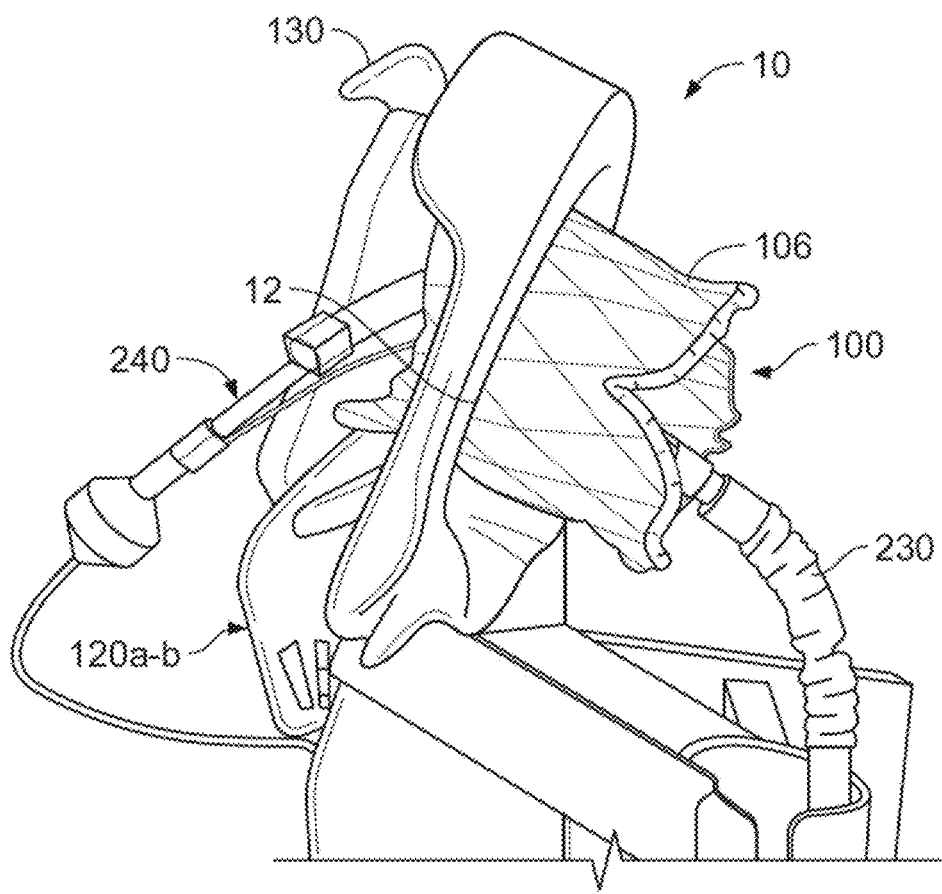

FIGS. 25 through 27 illustrate the release process of the portions of the valve 100 from the inner control catheter 240. As the portions of the valve 100 are released, those portions become engaged in the targeted native anatomical locations. The control wires and/or release pins for the anterior flaps 120a-b and the posterior flap 130 are released (as best seen in FIG. 26). In response, the anterior flaps 120a-b deploy into the RVOT and the posterior flap 130 deploys to the posterior area of the tricuspid valve 10 just inferior to the annulus 12. In addition, as the posterior flap 130 deploys, the one or more leaflet engagement members 140 engage with and capture/hold a portion of the native leaflet (e.g., the posterior leaflet 11p and/or the septal leaflet 11s) to provide migration resistance for the valve 100. At this stage, the posterior arm 150 and/or the anterior arm 160 (FIGS. 6-9) can also be deployed if the valve 100 includes a posterior arm 150 and/or an anterior arm 160. FIG. 27 shows the release of control wires that are coupled to the main body 106. In response, the main body 106 radially expands into contact and engagement with the annulus 12.

Figure 28:
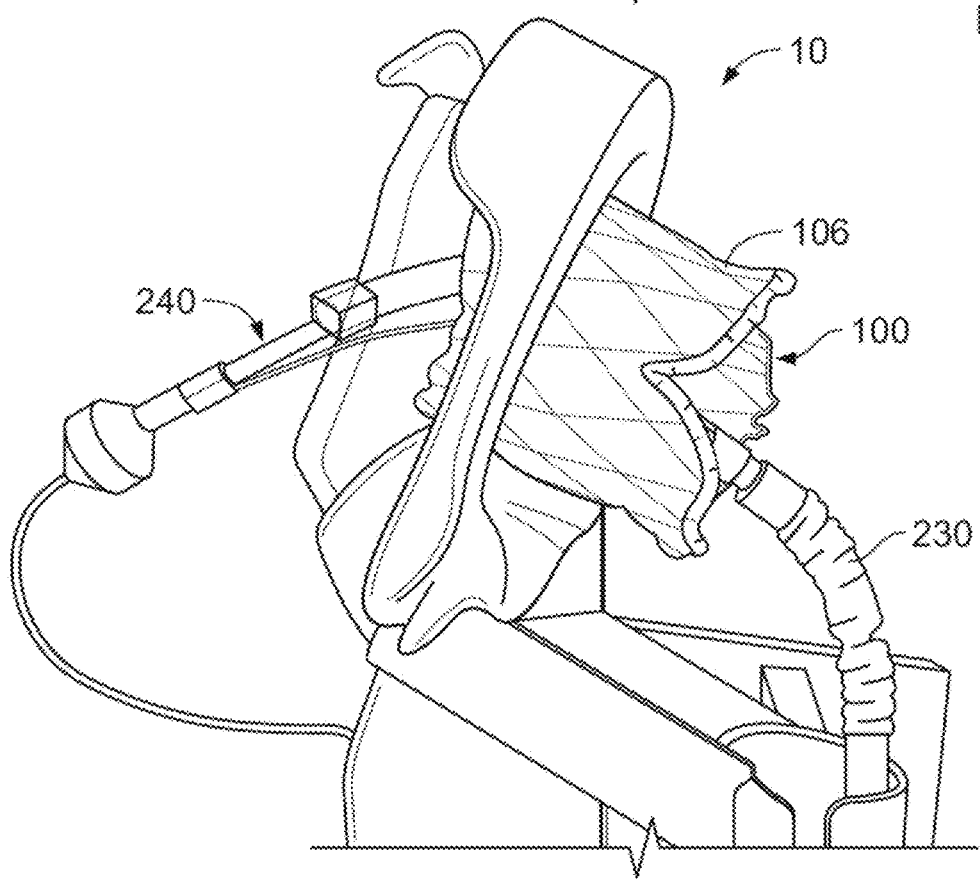
Figure 29:
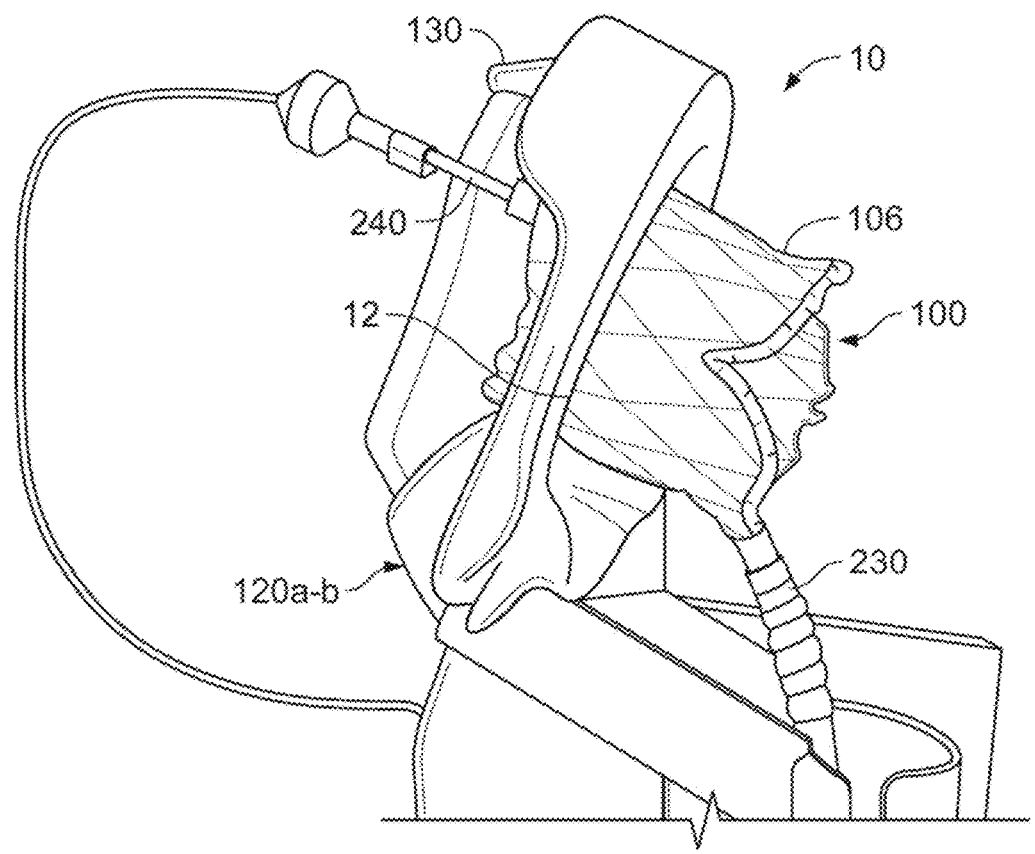
Figure 30:
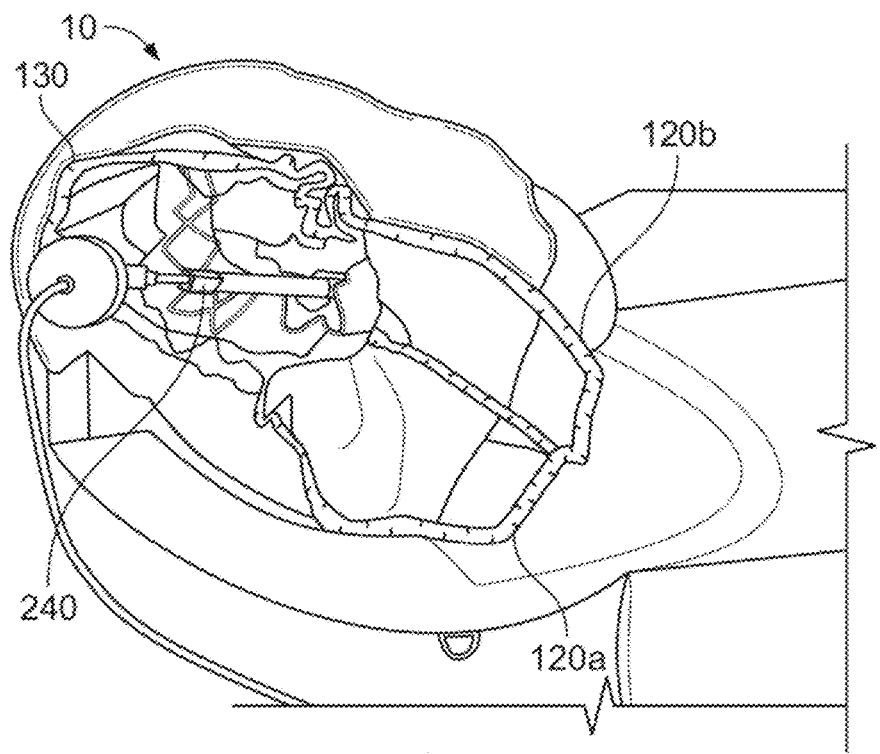

FIGS. 28 through 30 illustrate withdrawal of the deployment system 200. When the control wires are disengaged from the valve 100, the inner control catheter 240 and the middle deflectable catheter 230 can then be withdrawn, leaving the valve 100 engaged with the anatomy in and around the native tricuspid valve 100.

FIG. 31 illustrates another example prosthetic heart valve 300. The valve 300 is similar to the valve 100 described above, but is modified to be better suited for trans-femoral delivery (via the inferior vena cava) to the native tricuspid valve 10.

The valve 300 includes an ovular main body 306 that contains a circular occluder 310 that defines a central axis 301. The occluder 310 extends between an inflow end and an outflow end portion of the main body 306, and includes valve leaflets in an arrangement that: (i) allows blood flow through the occluder 310 in a direction from the inflow end portion toward the outflow end portion along a central axis 301 of the occluder 310 and (ii) prevents blood flow through the occluder 310 in a direction from the outflow end portion toward the inflow end portion. The valve 300 also includes a first anterior flap 320a extending from the outflow end portion of the main body 306 in a first direction that is transverse to the central axis 301, and a second anterior flap 320b also extending from the outflow end portion in the first direction. The valve 300 also includes a first posterior flap 330a extending from the outflow end portion of the main body 306 in a second direction that is opposite of the first direction, and a second posterior flap 330b also extending from the outflow end portion in the second direction. A passageway 332 (e.g., for a pacemaker lead as described above) is defined between the first and second posterior flaps 330a-b. In contrast to the valve 100, the first and second posterior flaps 330a-b of the valve 300 extend from the outflow end portion of the main body 306 farther (a greater distance) than the first and second anterior flaps 320a-b. This arrangement biases the main body 306 toward the anterior portion of the annulus 12 (refer to FIG. 10), which is different from the valve 100 which is biased toward the posterior portion of the annulus 12 (refer to FIG. 12).

FIGS. 32-37 schematically illustrate a series of steps for deploying the heart valve 300 (as described herein in any of its variations) into the heart 1 using the heart valve deployment system 200 (e.g., refer to FIGS. 17 and 18). These figures illustrate a trans-femoral vein approach to the native tricuspid valve 10 (via the inferior vena cava; "IVC").

Figure 32:
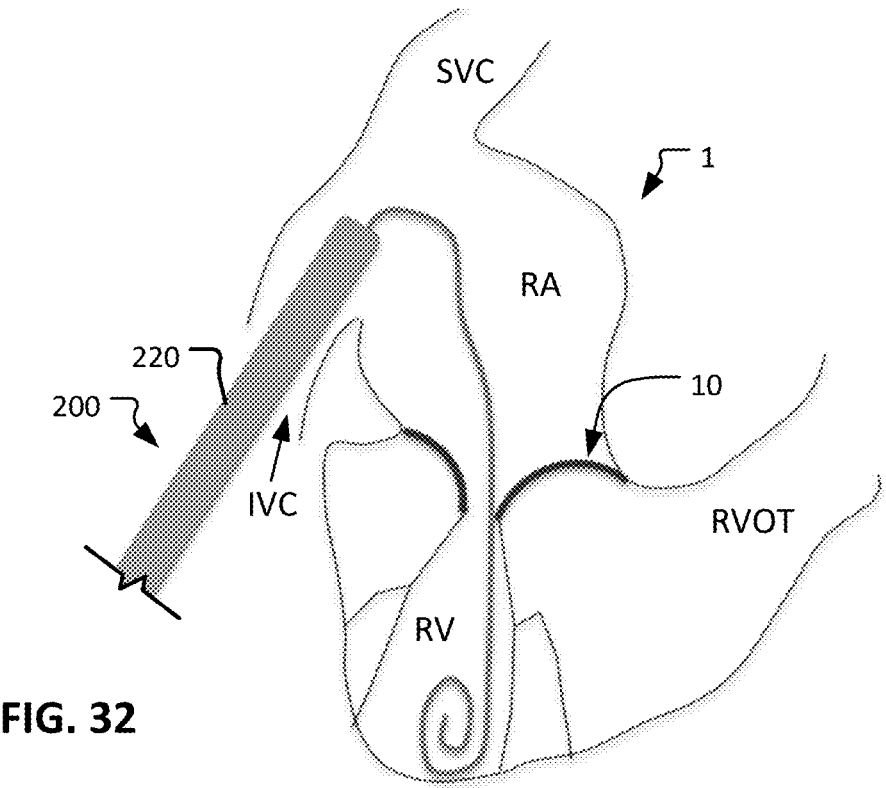
FIGS. 32-37 schematically depict an example trans-femoral method of deploying the prosthetic heart valve of FIG. 31 using the prosthetic heart valve deployment system of FIG. 17.

FIG. 32 illustrates the advancement of the deployment system 200 toward the right atrium ("RA") via the IVC. The outer sheath catheter 220 (containing the heart valve 300 in its low-profile delivery configuration) can be advanced over a previously placed guidewire that extends into the right ventricle ("RV") via the native tricuspid valve 10.

Figure 33:
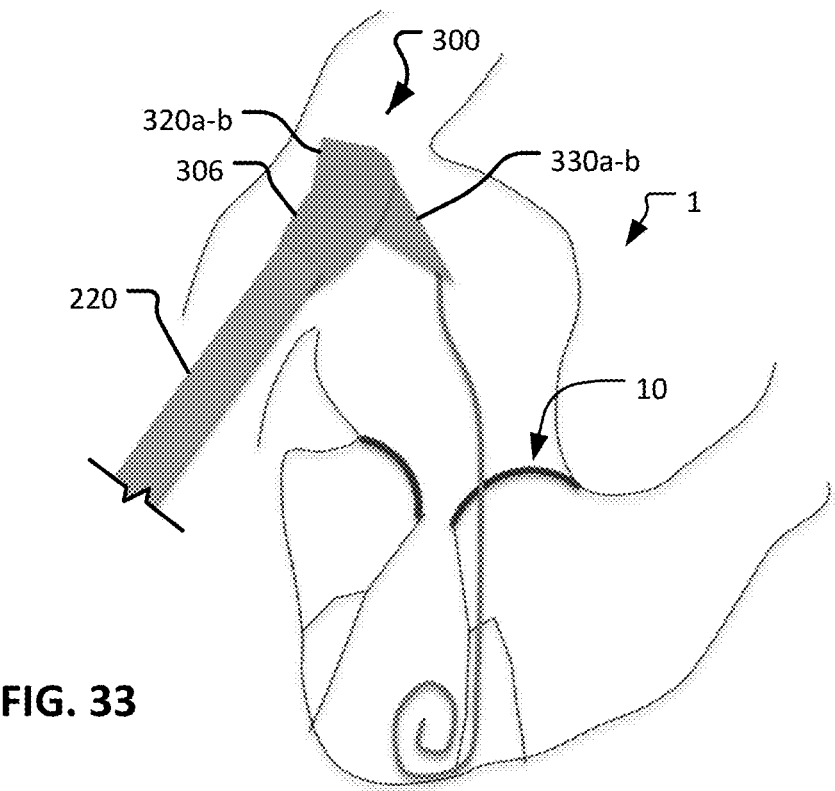

FIG. 33 illustrates the emergence in the RA of the heart valve 300 from the outer sheath catheter 220 (e.g., by pulling the outer sheath catheter 220 proximally and/or by distally advancing the middle deflectable catheter 230 and inner control catheter 240).

Figure 34:
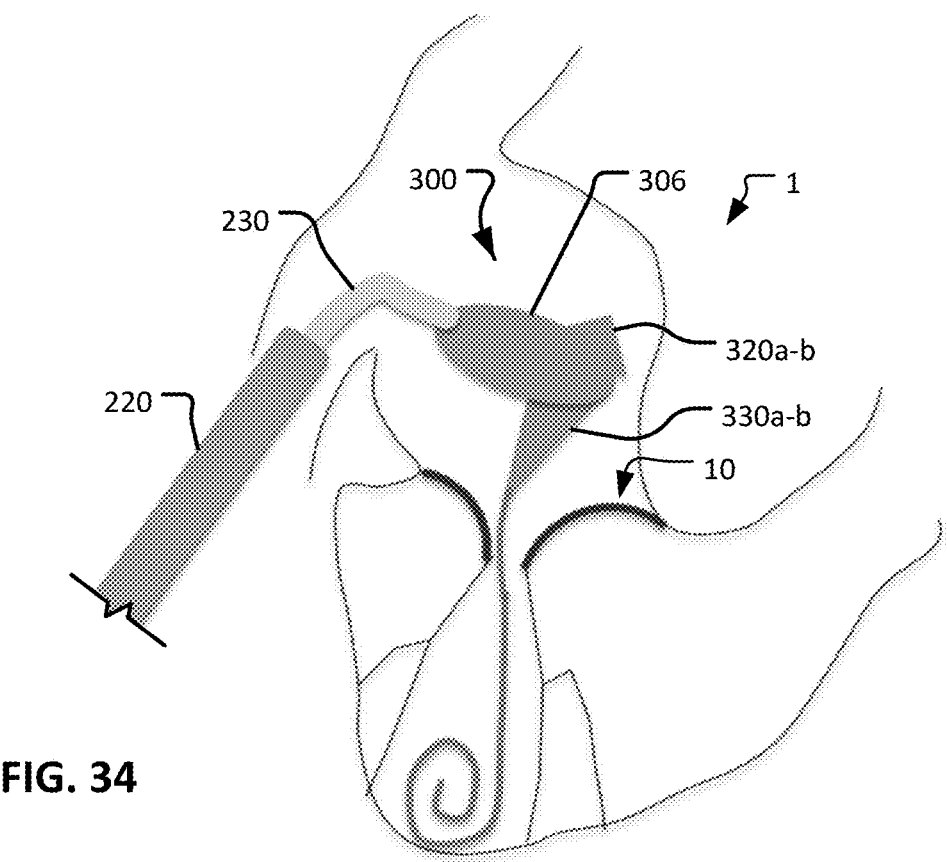
Figure 35:
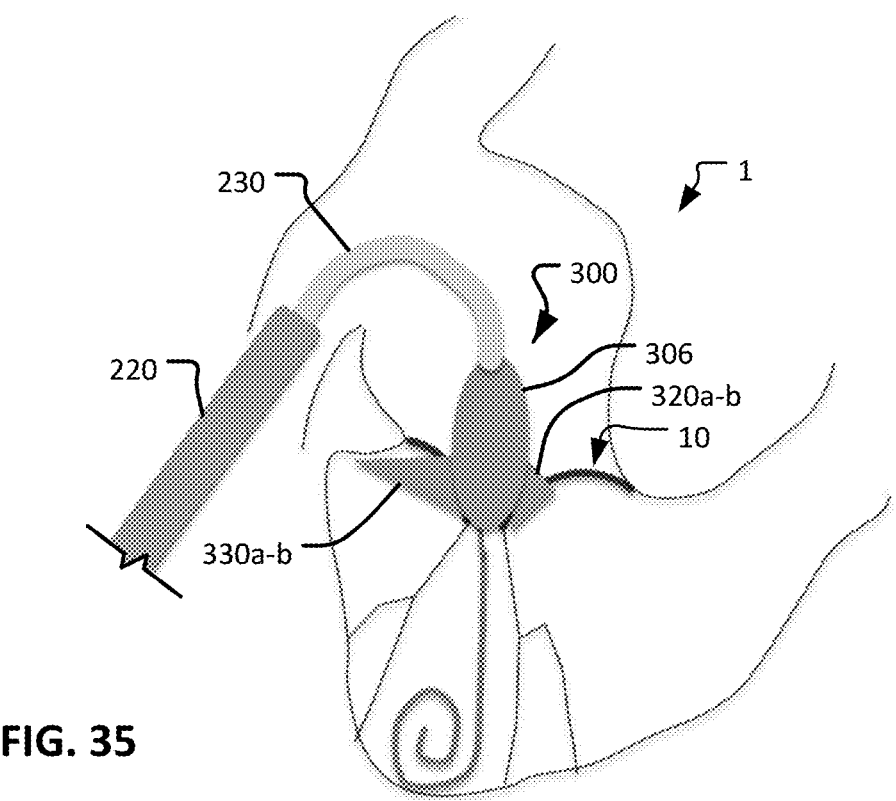

FIGS. 34 and 35 illustrate the advancement of the heart valve 300 into position for engagement with the native tricuspid valve 10. To accomplish this, the middle deflectable catheter 230 and inner control catheter 240 are both curved. That is, the inner control catheter 240 is naturally curved because of its curved portion 242, and the middle deflectable catheter 230 is selectively deflected by a clinician operator who is performing the procedure.

Figure 36:
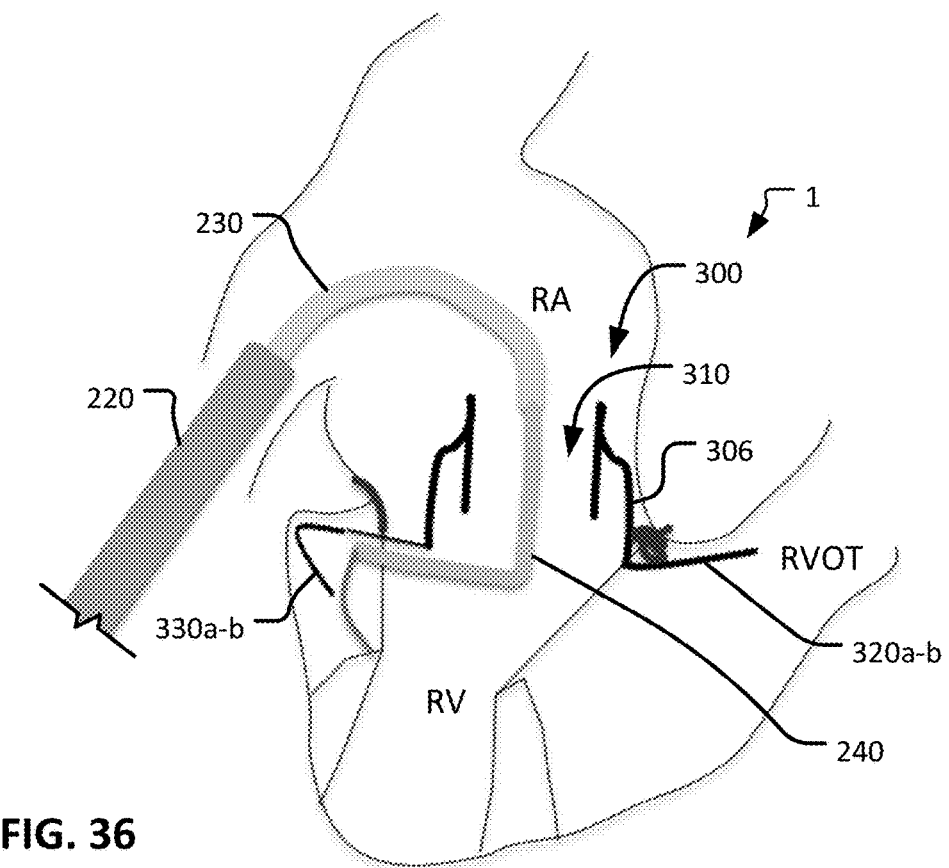

FIG. 36 illustrates the release of the heart valve 300 from the inner control catheter 240, and the resulting expansion/deployment of the heart valve 300 into engagement at the location of the native tricuspid valve 10. The release of the various components/regions of the heart valve 300 can be performed in a controlled manner by manual manipulation of the one or more control wires and/or release pins 244 (FIG. 18) by the clinician operator. The release of the heart valve 300 from the inner control catheter 240 results in the expansion of the main body 306, the anterior flaps 320a-b, and the posterior flaps 330a-b into engagement with the anatomy of the native tricuspid valve 10, the RV, and the RVOT.

Figure 37:
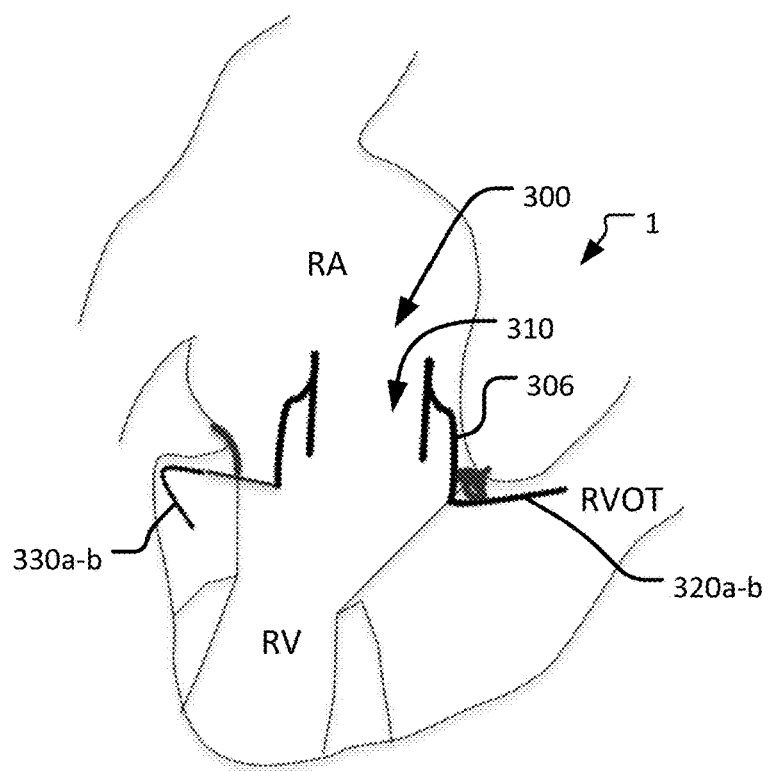

Lastly, FIG. 37 illustrates the implanted heart valve 300 in engagement with the heart 1 and functioning as a prosthetic tricuspid valve between the RA and the RV. The deployment system 200 and guidewire have been withdrawn. It can be seen here (and in the top view of FIG. 31) that the heart valve 300 is positioned such that the main body 306 is positionally biased toward the anterior portion of the annulus 12 (refer to FIG. 10), which is adjacent the RVOT. Accordingly (and as shown in FIG. 31), the laterally-extending first and second posterior flaps 330a-b help to cover and fluidly seal the native tricuspid valve opening within the annulus 12, which is not circular in this example (e.g., with the native valve opening being oblong, oval, or irregularly shaped). In other words, in combination with the main body 306 of the valve 300, the first and second posterior flaps 330a-b (and, in some cases, the laterally-extending anterior anchoring flaps 320a-b to a lesser extent) help to cover/occlude and fluidly seal the native tricuspid valve opening which is not circular in some cases. In addition, the end portions of the first and second posterior flaps 330a-b extend into engagement with the posterior shelf 11 (FIG. 4) and/or with the wall of the RV just inferior to the annulus 12 to provide anchoring and migration resistance. Accordingly, the first and second posterior flaps 330a-b perform both sealing and anchorage.

Figure 38:
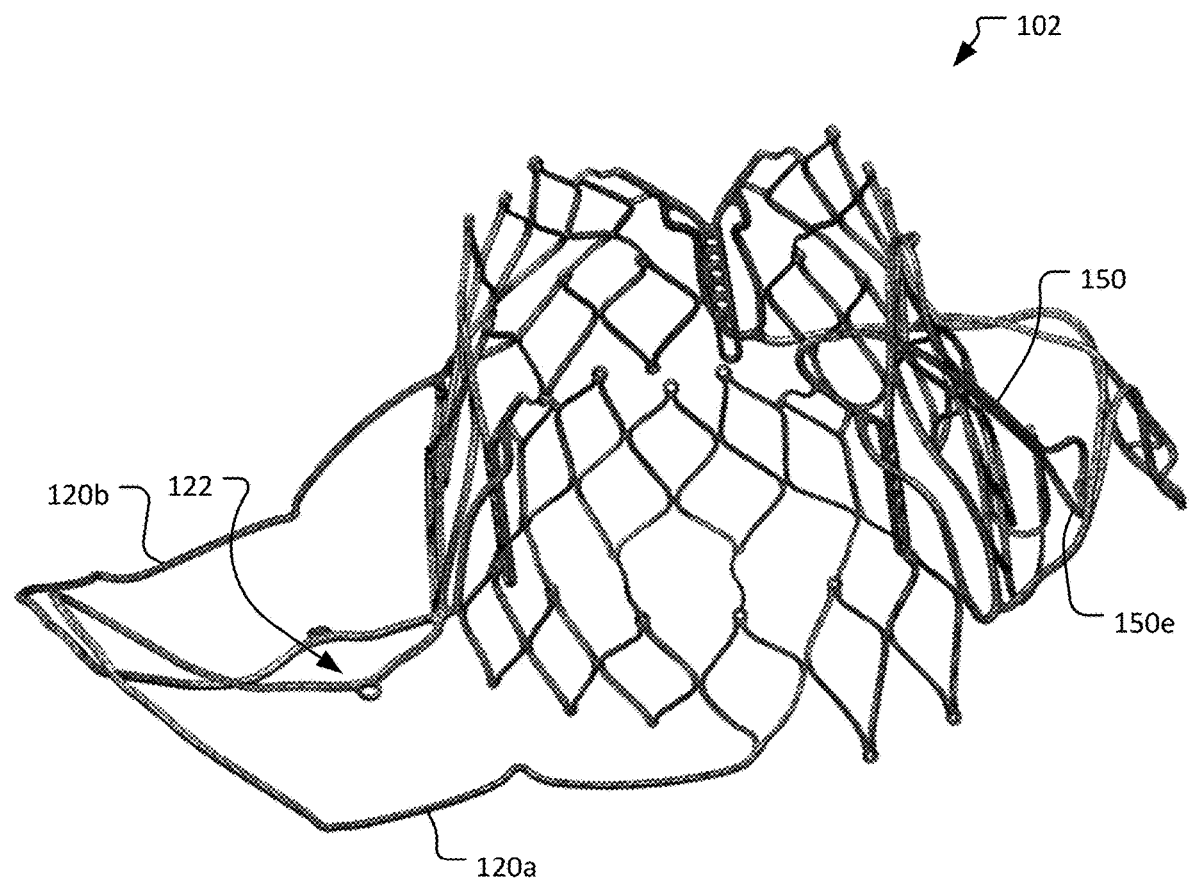
FIG. 38 is a perspective view of an example frame that can be used for the prosthetic heart valves described herein.
Figure 39:
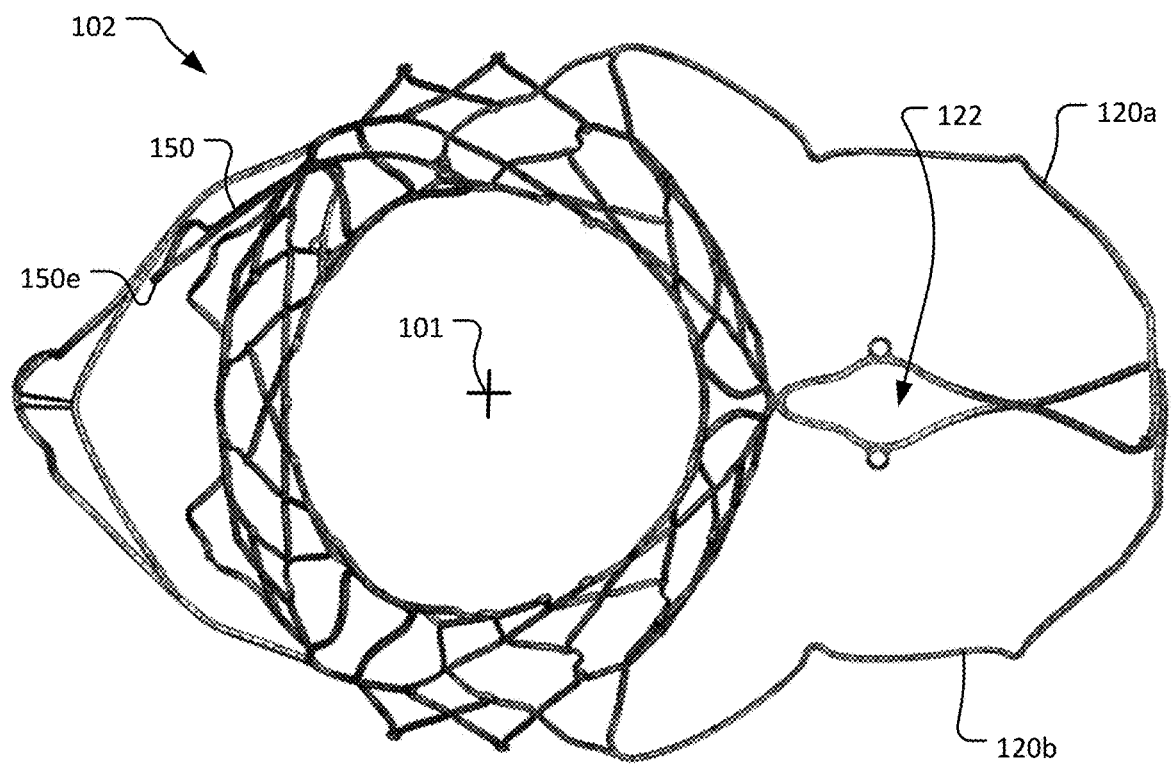
FIG. 39 is a top view of the frame of FIG. 38.
Figure 40:
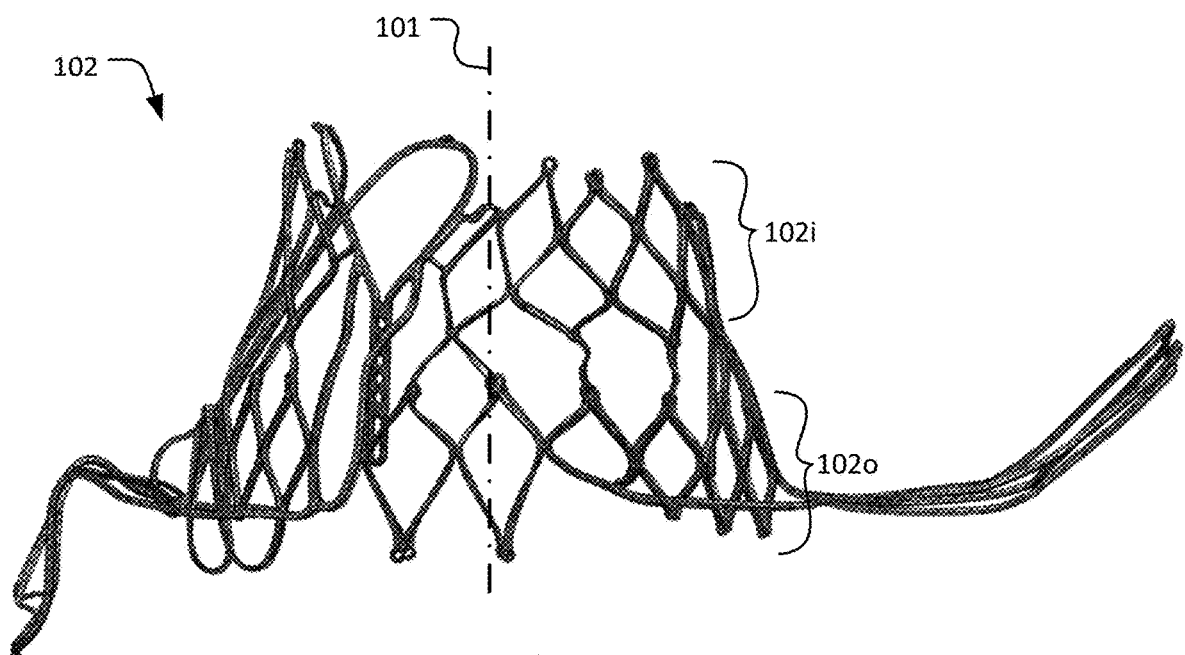
FIG. 40 is a side view of the frame of FIG. 38.

FIGS. 38-40 illustrate the frame 102 that can be used in some embodiments of the prosthetic heart valves described herein. The frame 102 has a cellular construction that provides mechanical support for the shape and structures of the prosthetic heart valves. In some embodiments, the frame 102 is made from nitinol (NiTi), stainless steel, cobalt chromium, MP35N, titanium, polymeric materials, other biocompatible materials, or any combination thereof. Some or all parts of the frame 102 may be covered (e.g., by the covering 104 described above). In some embodiments, the frame 102 can be made of a laser cut, expanded, and shape-set material. The frame 102 is self-expanding in some embodiments. In some embodiments, the precursor material is tubular NiTi, a NiTi sheet, or other suitable types of precursor materials.

In this example, the frame 102 includes the optional posterior arm 150 with the free end 150e. The posterior arm 150 can also be referred to as a "diastolic anchoring tab," because the posterior arm 150 helps to prevent migration of the prosthetic heart valve toward the right ventricle during diastole. In this example, the frame 102 does not include the anterior arm 160 (e.g., see FIG. 9). However, in some embodiments the anterior arm 160 is included as part of the frame 102.

In this example, the frame 102 does not include the frame portions 128a and 128b (e.g., see FIG. 9). However, in some embodiments the frame portions 128a and 128b are included as part of the frame 102.

As best seen in FIG. 40, the frame 102 includes an inflow end portion 102i and an outflow end portion 102o. In the depicted embodiment, the cellular structure of the inflow end portion 102i and an outflow end portion 102o differ from each other. In particular, the size of the cells that make up the inflow end portion 102i are smaller than the size of the cells that make up the outflow end portion 102o. For example, the cells of the inflow end portion 102i have a shorter longitudinal length (e.g., measured longitudinally parallel to the longitudinal axis 101) than the cells of the outflow end portion 102o. Said another way, the cells of the outflow end portion 102o are longer when measured along the longitudinal direction of the frame 102 than the cells of the inflow end portion 102i.

The differences in the sizes of the cells of the inflow end portion 102i as compared to the cells of the outflow end portion 102o causes the frame 102 to advantageously have different structural characteristics along the longitudinal length of the frame 102. For example, the inflow end portion 102i of the frame 102 is structurally stiffer than the outflow end portion 102o, particularly as related to radially directed forces. Conversely, the outflow end portion 102o of the frame 102 is structurally more flexible than the inflow end portion 102i. Moreover, the structures of the anterior flaps 120a-b are very flexible because of the anterior flaps 120a-b are primarily made of large open areas within peripheral frame members (e.g., see FIG. 39).

It can be advantageous for the inflow end portion 102i of the frame 102 to be structurally stiff. For example, such stiffness can help to maintain the circular cross-sectional shape of the occluder of the prosthetic valve (e.g., the occluder 110 shown in FIGS. 6-8) while the heart muscle contracts to pump blood. Keeping such a circular cross-sectional shape of the occluder can serve to ensure that the leaflets of the occluder maintain their relative orientations in a predictable way. This can beneficially provide robust coaptation between the leaflets to mitigate the occurrence of regurgitation through the occluder, for example.

It can be advantageous for the outflow end portion 102o of the frame 102 and the anterior flaps 120a-b to be structurally flexible. For example, such flexibility can beneficially mitigate the amount of force from the frame 102 that is exerted onto the anatomy of the heart. In particular, having a flexible outflow end portion 102o and flexible anterior flaps 120a-b reduces or eliminates forces from the frame 102 from being applied to certain sensitive anatomical areas such as the AV node, the right coronary artery, and the annulus of the heart valve, to provide a few examples.

Figure 41:
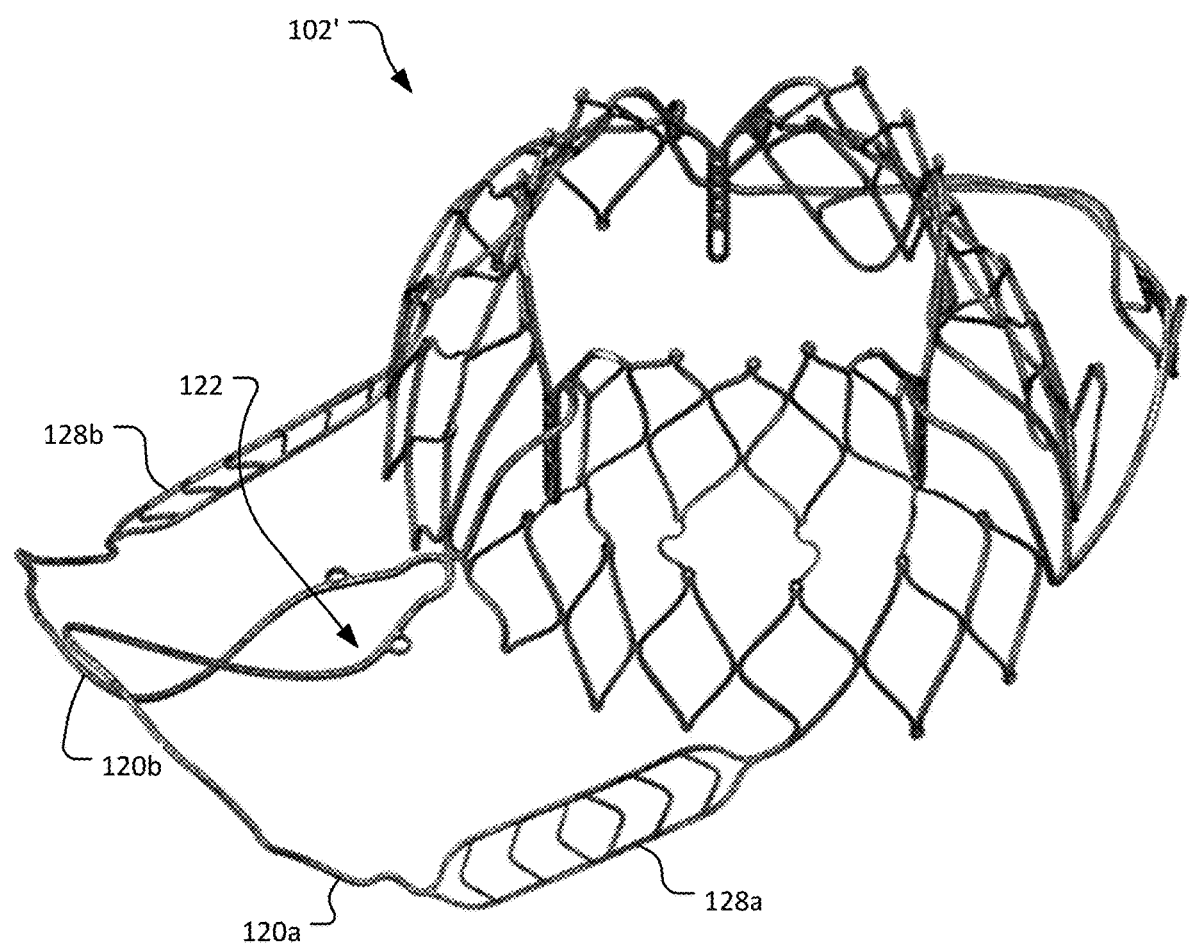
FIG. 41 is a perspective view of another example frame that can be used for the prosthetic heart valves described herein.
Figure 42:
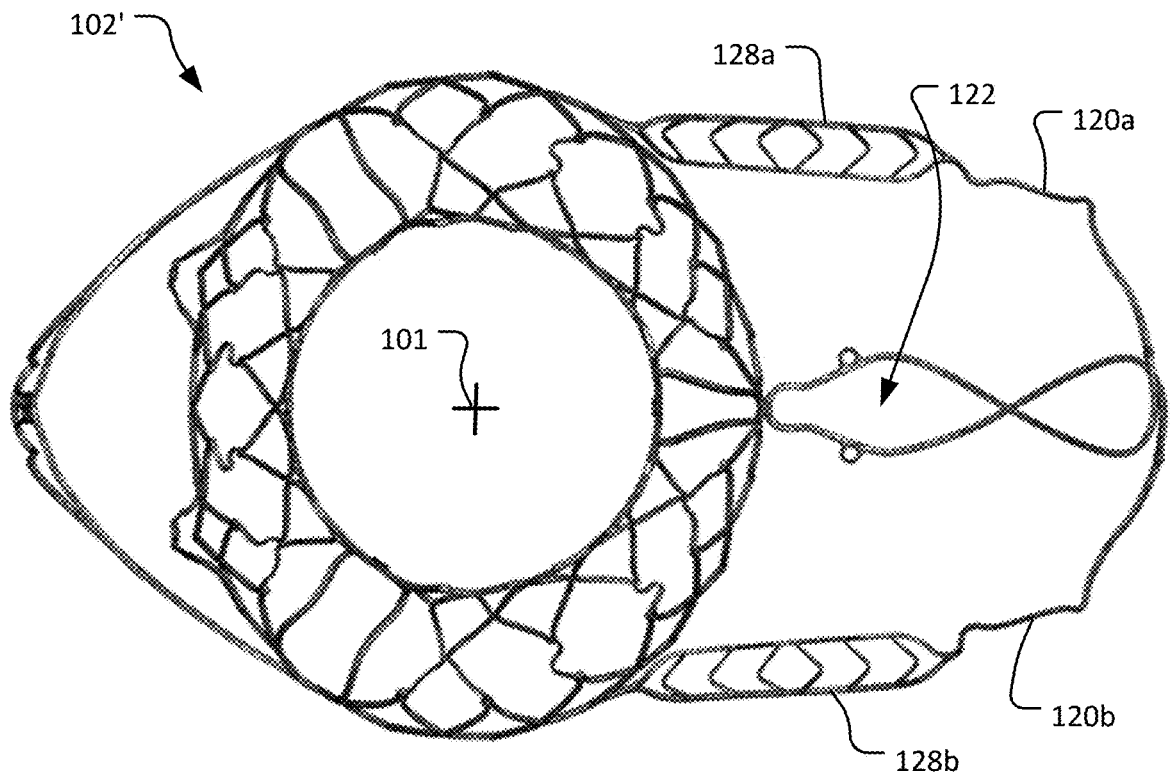
FIG. 42 is a top view of the frame of FIG. 41.
Figure 43:
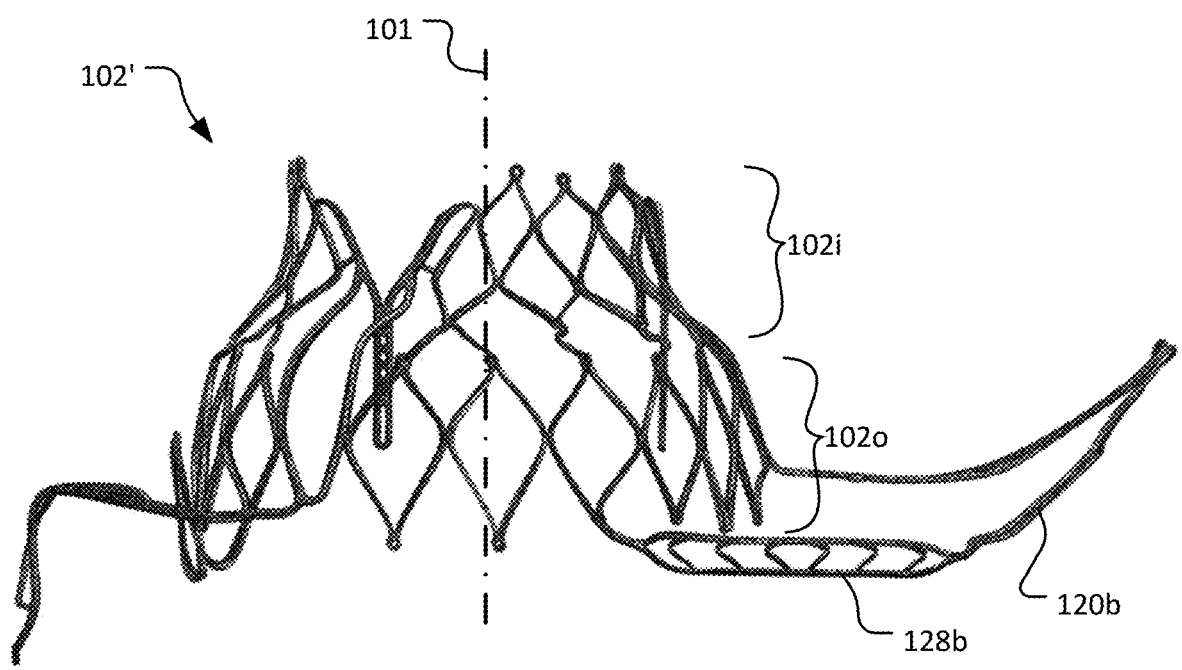
FIG. 43 is a side view of the frame of FIG. 41.

FIGS. 41-43 illustrate another example frame 102' that can be used in some embodiments of the prosthetic heart valves described herein. This embodiment is different from the frame 102 in that the frame 102' includes the frame portions 128a and 128b and does not include the posterior arm 150 (and also does not include an anterior arm 160). It should be understood that such features can be mixed and matched in any desired combination.

The frame 102' shares the cell-size characteristics of the frame 102 as described above. That is, the cells that make up the inflow end portion 102i are smaller and stiffer than the cells that make up the outflow end portion 102o. The cells of the anterior flaps 120a-b have the largest size (making them the most flexible portion of the frame 102').

Alternative methods of achieving the variable stiffness characteristics described above are also contemplated. For example, the strut widths and/or thicknesses of different portions of the frame 102 could be different.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment in part or in whole. Conversely, various features that are described in the context of a single embodiment can also be implemented in multiple embodiments separately or in any suitable subcombination. Moreover, although features may be described herein as acting in certain combinations and/or initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. Although a number of implementations have been described in detail above, other modifications are possible. For example, the steps depicted in the figures do not require the particular order shown, or sequential order, to achieve desirable results. In addition, other steps may be provided, or steps may be eliminated, from the described flows, and other components may be added to, or removed from, the described systems. Accordingly, other implementations are within the scope of the following claims.

What is claimed is:

1. A prosthetic heart valve deployment system comprising:
   an outer sheath catheter defining a first lumen;
   a middle deflectable catheter slidably disposed in the first lumen and defining a second lumen, the middle deflectable catheter comprising a selectively deflectable distal end portion with at least one plane of deflection; and
   an inner control catheter slidably disposed in the second lumen and including one or more control wires that configure the inner control catheter to releasably couple with a prosthetic heart valve,
   wherein the inner control catheter includes a distal end portion that elastically transitions to a naturally curved configuration when the inner control catheter converts from being radially constrained to being radially unconstrained, and
   wherein the distal end portion defines an interior angle of less than 135 degrees when in the naturally curved configuration.

2. The prosthetic heart valve deployment system of claim 1, wherein the distal end portion of the inner control catheter is curved by less than 200 when radially constrained in the first lumen.

3. The prosthetic heart valve deployment system of claim 1, wherein, when the selectively deflectable distal end portion of the middle deflectable catheter is deflected, the inner control catheter and the middle deflectable catheter in combination are curved and define an interior angle between 0° and 30° relative to an axis of the outer sheath.

4. The prosthetic heart valve deployment system of claim 1, wherein, when the selectively deflectable distal end portion of the middle deflectable catheter is deflected, the inner control catheter and the middle deflectable catheter in combination are curved and define an interior angle between 300 and 60° relative to an axis of the outer sheath.

5. The prosthetic heart valve deployment system of claim 1, wherein the selectively deflectable distal end portion is deflectable in a same plane as a plane of the naturally curved distal end portion of the inner control catheter.

6. The prosthetic heart valve deployment system of claim 1, wherein the inner control catheter defines a third lumen for slidably receiving a guidewire.

7. A prosthetic heart valve comprising:
   a frame member comprising:
      an inflow end portion comprised of first cells;
      an outflow end portion comprised of second cells;
      an occluder extending between the inflow end and outflow end portions and comprising valve leaflets attached to the frame member in an arrangement that: (i) allows blood flow through the occluder in a direction from the inflow end portion toward the outflow end portion along a central axis of the occluder and (ii) prevents blood flow through the occluder in a direction from the outflow end portion toward the inflow end portion;
   a first anterior flap extending from the outflow end portion in a first direction that is transverse to the central axis; and
   a second anterior flap extending from the outflow end portion in the first direction,
   wherein the first cells are smaller than the second cells, and wherein the first and second anterior flaps define open spaces that are larger than open spaces defined by the first cells and larger than open spaced defined by the second cells.

8. The prosthetic heart valve of claim 7, wherein a longitudinal length of the first cells are shorter than a longitudinal length of the second cells.

9. The prosthetic heart valve of claim 7, wherein a flexibility of the outflow end portion is greater than a flexibility of the inflow end portion.

10. The prosthetic heart valve of claim 7, wherein a transverse cross-sectional shape of the inflow end portion is circular, and wherein a transverse cross-sectional shape of the outflow end portion is oval shaped.

11. The prosthetic heart valve of claim 7, further comprising a posterior flap extending from the outflow end portion in a second direction that is opposite of the first direction.

12. The prosthetic heart valve of claim 11, wherein an open space defined by the posterior flap is larger than open spaces defined by the first cells and larger than open spaced defined by the second cells.

13. The prosthetic heart valve of claim 11, further comprising a posterior arm extending from the inflow end portion in the second direction.

14. A prosthetic heart valve comprising:
a frame member comprising:
an inflow end portion comprised of first cells;
an outflow end portion comprised of second cells;
an occluder extending between the inflow end and outflow end portions and comprising valve leaflets attached to the frame member in an arrangement that: (i) allows blood flow through the occluder in a direction from the inflow end portion toward the outflow end portion along a central axis of the occluder and (ii) prevents blood flow through the occluder in a direction from the outflow end portion toward the inflow end portion;
a first anterior flap extending from the outflow end portion in a first direction that is transverse to the central axis; and
a second anterior flap extending from the outflow end portion in the first direction,
wherein the first cells are smaller than the second cells, and
wherein a transverse cross-sectional shape of the inflow end portion is circular, and wherein a transverse cross-sectional shape of the outflow end portion is oval shaped.

15. The prosthetic heart valve of claim 14, wherein a longitudinal length of the first cells are shorter than a longitudinal length of the second cells.

16. The prosthetic heart valve of claim 14, wherein the first and second anterior flaps define open spaces that are larger than open spaces defined by the first cells and larger than open spaced defined by the second cells.

17. The prosthetic heart valve of claim 14, wherein a flexibility of the outflow end portion is greater than a flexibility of the inflow end portion.

18. The prosthetic heart valve of claim 14, further comprising a posterior flap extending from the outflow end portion in a second direction that is opposite of the first direction.

19. The prosthetic heart valve of claim 18, wherein an open space defined by the posterior flap is larger than open spaces defined by the first cells and larger than open spaced defined by the second cells.

20. The prosthetic heart valve of claim 18, further comprising a posterior arm extending from the inflow end portion in the second direction.

21. A prosthetic heart valve comprising:
a frame member comprising:
an inflow end portion comprised of first cells;
an outflow end portion comprised of second cells;
an occluder extending between the inflow end and outflow end portions and comprising valve leaflets attached to the frame member in an arrangement that: (i) allows blood flow through the occluder in a direction from the inflow end portion toward the outflow end portion along a central axis of the occluder and (ii) prevents blood flow through the occluder in a direction from the outflow end portion toward the inflow end portion;
a first anterior flap extending from the outflow end portion in a first direction that is transverse to the central axis;
a second anterior flap extending from the outflow end portion in the first direction; and
a posterior flap extending from the outflow end portion in a second direction that is opposite of the first direction,
wherein the first cells are smaller than the second cells, and
wherein an open space defined by the posterior flap is larger than open spaces defined by the first cells and larger than open spaced defined by the second cells.

22. The prosthetic heart valve of claim 21, wherein a longitudinal length of the first cells are shorter than a longitudinal length of the second cells.

23. The prosthetic heart valve of claim 21, wherein the first and second anterior flaps define open spaces that are larger than open spaces defined by the first cells and larger than open spaced defined by the second cells.

24. The prosthetic heart valve of claim 21, wherein a flexibility of the outflow end portion is greater than a flexibility of the inflow end portion.

25. The prosthetic heart valve of claim 21, wherein a transverse cross-sectional shape of the inflow end portion is circular, and wherein a transverse cross-sectional shape of the outflow end portion is oval shaped.

26. The prosthetic heart valve of claim 21, further comprising a posterior arm extending from the inflow end portion in the second direction.

* * * * *